(12) United States Patent
Pamichev et al.

(10) Patent No.: US 9,445,824 B2
(45) Date of Patent: Sep. 20, 2016

(54) METHOD AND APPARATUS FOR PERFORMING ARTHROSCOPIC MICROFRACTURE SURGERY

(71) Applicant: Pivot Medical, Inc., Sunnyvale, CA (US)

(72) Inventors: Chris Pamichev, Sunnyvale, CA (US); Julian Nikolchev, Portola Valley, CA (US); James R. Flom, San Carlos, CA (US); Lynette Ross, Mountain View, CA (US); Matthew Frushell, Danville, CA (US); William Kaiser, San Jose, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 206 days.

(21) Appl. No.: 13/848,335

(22) Filed: Mar. 21, 2013

(65) Prior Publication Data

US 2014/0074094 A1    Mar. 13, 2014

Related U.S. Application Data

(63) Continuation of application No. 12/437,955, filed on May 8, 2009, now Pat. No. 8,409,230.

(60) Provisional application No. 61/126,911, filed on May 8, 2008.

(51) Int. Cl.
*A61B 17/16* (2006.01)
*A61B 17/32* (2006.01)
*A61B 17/92* (2006.01)

(52) U.S. Cl.
CPC ....... *A61B 17/1604* (2013.01); *A61B 17/1631* (2013.01); *A61B 17/1615* (2013.01); *A61B 17/320068* (2013.01); *A61B 2017/320028* (2013.01); *A61B 2017/320032* (2013.01); *A61B 2017/922* (2013.01)

(58) Field of Classification Search
CPC .......... A61B 17/1615; A61B 17/1617; A61B 17/1631
See application file for complete search history.

(56) References Cited

U.S. PATENT DOCUMENTS

| | | | |
|---|---|---|---|
| 3,176,395 A | 4/1965 | Warner et al. | |
| 2004/0147932 A1 | 7/2004 | Burkinshaw et al. | |
| 2006/0235419 A1 | 10/2006 | Steinwachs et al. | |
| 2007/0123889 A1* | 5/2007 | Malandain et al. | 606/79 |
| 2008/0188854 A1* | 8/2008 | Moser | 606/80 |
| 2010/0268234 A1* | 10/2010 | Aho | A61B 17/1617 606/80 |

* cited by examiner

*Primary Examiner* — David Bates
*Assistant Examiner* — Olivia C Chang
(74) *Attorney, Agent, or Firm* — Pandiscio & Pandiscio

(57) ABSTRACT

A microfracture instrument for applying microfracture therapy to a bone, the microfracture instrument comprising:
an elongated shaft comprising a distal end and a proximal end;
a needle comprising a body terminating in at least one sharp point, the needle being movably mounted to the distal end of the shaft for movement between an extended position for engaging the bone with the at least one sharp point of the needle and a retracted position for withdrawing the at least one sharp point of the needle from the bone; and
a drive shaft movably mounted to the elongated shaft, the drive shaft being connected to the body of the needle so that movement of the drive shaft relative to the elongated shaft moves the needle between its extended position and its retracted position.

4 Claims, 35 Drawing Sheets

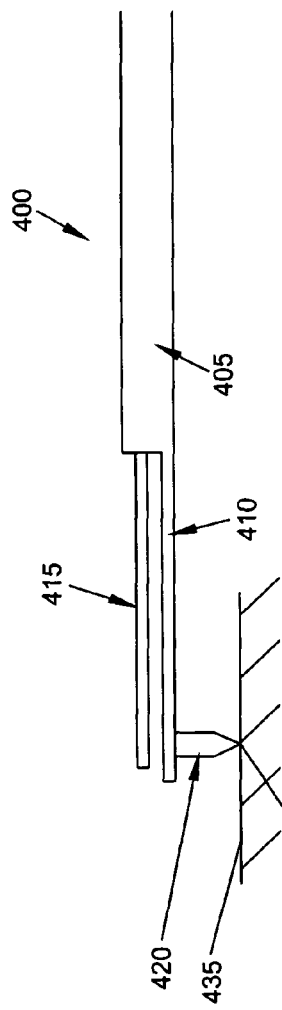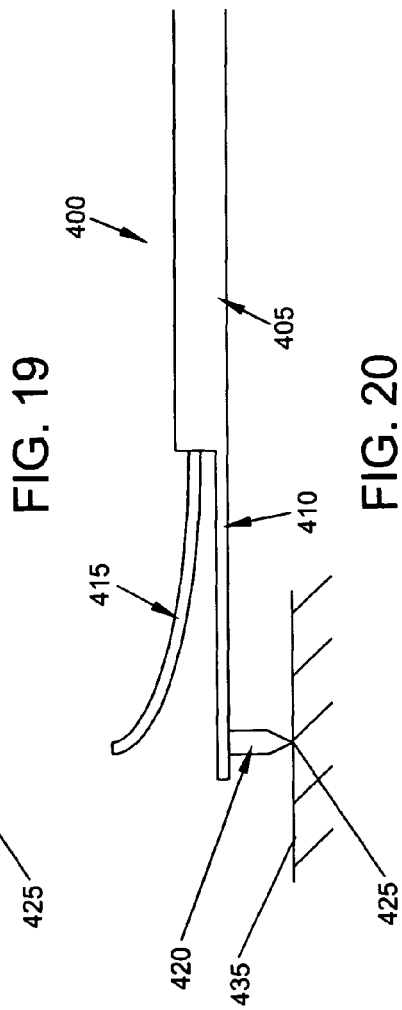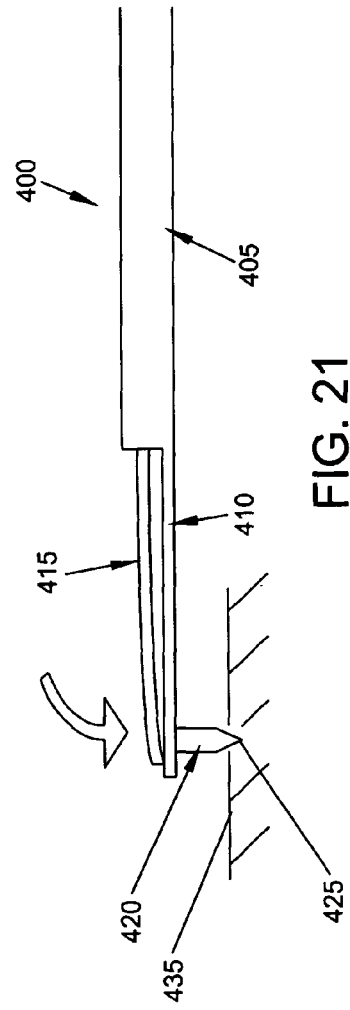

At Rest Condition
Trigger Released
Cocking Knob Down

Disposable Beam, Needle And Cocking Bar
(Bottom View, Uncocked Condition)

Transitioning From At Rest Condition To Cocked Condition
Trigger Released
Cocking Knob Starting To Turn Upward Fully Cocked Condition
Trigger Released
Cocking Knob Turned Upward Preparing To Recock
Trigger Depressed
Cocking Knob Starting To Turn Downwards

METHOD AND APPARATUS FOR PERFORMING ARTHROSCOPIC MICROFRACTURE SURGERY

REFERENCE TO PENDING PRIOR PATENT APPLICATIONS

This patent application is a continuation of pending prior U.S. patent application Ser. No. 12/437,955, filed May 8, 2009 by Chris Pamichev et al. for METHOD AND APPARATUS FOR PERFORMING ARTHROSCOPIC MICROFRACTURE SURGERY, which in turn claims benefit of prior U.S. Provisional patent application Ser. No. 61/126,911, filed May 8, 2008 by Chris Pamichev et al. for METHOD AND APPARATUS FOR PERFORMING ARTHROSCOPIC MICROFRACTURE SURGERY.

The above-identified patent applications are hereby incorporated herein by reference.

FIELD OF THE INVENTION

This invention relates to methods and apparatus for performing orthopedic surgery in general, and more particularly to methods and apparatus for performing arthroscopic microfracture surgery.

BACKGROUND OF THE INVENTION

Articular cartilage is a smooth, resilient tissue which covers the opposing ends of bones and facilitates the smooth movement of the bones relative to one another. However, when articular cartilage is damaged (e.g., through injury or prolonged wear), subsequent motion of the bones tends to increase that damage, ultimately causing the cartilage to wear away completely. When this occurs, the bones rub directly against one another, typically resulting in substantial pain for the patient and reduced mobility of the joint. In many cases, such damage to articular cartilage can lead to osteoarthritis.

Microfracture surgery is an orthopedic procedure which can help to restore articular cartilage. More particularly, microfracture surgery creates tiny fractures in the cortical bone bed disposed immediately below the damaged articular cartilage. These fractures permit blood and bone marrow to seep out of the underlying cancellous bone and essentially create blood clots which release cartilage-building cells. These cartilage-building cells then result in the formation of replacement cartilage.

To date, microfracture surgery is typically performed using a small, sharp pick or awl to create the small microfracture holes in the cortical bone. However, such picks or awls are generally used by driving them longitudinally, e.g., with a hammer or mallet, thereby requiring substantially direct linear access to the bone surface which is to receive the microfracture therapy. Furthermore, where the microfracture must be created in a bone surface which is not substantially aligned with the angle of access, it can be difficult to generate the forces required for the pick or awl to penetrate the hard cortical bone and release blood and bone marrow from the underlying cancellous bone.

In many cases, e.g., certain sites on the lower femur, such direct linear access to the microfracture site may be readily available. However, in other cases, intervening anatomical structures may make it difficult or impossible to use a conventional pick or awl to perform the microfracture surgery on the bone. This is particularly true where the microfracture surgery is to be performed arthroscopically.

By way of example but not limitation, it can be difficult or even impossible to arthroscopically perform microfracture therapy on the acetabular cup of the hip using a conventional pick or awl, given the anatomical constraints typically imposed in arthroscopic hip surgery.

The present invention is intended to provide a novel method and apparatus for performing arthroscopic microfracture surgery, particularly in locations where it is difficult to utilize a conventional pick or awl in the microfracture surgery.

SUMMARY OF THE INVENTION

The present invention provides a novel method and apparatus for performing arthroscopic microfracture surgery. The novel apparatus permits the microfracture therapy to be applied to a bone surface even where that bone surface is set at an angle to the axis of approach and/or where it might otherwise be difficult or impossible to use a conventional pick or awl to perform the microfracture surgery.

In one form of the present invention, there is provided a microfracture instrument for applying microfracture therapy to a bone, the microfracture instrument comprising:
 an elongated shaft comprising a distal end and a proximal end;
 a needle comprising a body terminating in at least one sharp point, the needle being movably mounted to the distal end of the shaft for movement between an extended position for engaging the bone with the at least one sharp point of the needle and a retracted position for withdrawing the at least one sharp point of the needle from the bone; and
 a drive shaft movably mounted to the elongated shaft, the drive shaft being connected to the body of the needle so that movement of the drive shaft relative to the elongated shaft moves the needle between its extended position and its retracted position.

In another form of the present invention, there is provided a microfracture instrument for applying microfracture therapy to a bone, the microfracture instrument comprising:
 an elongated shaft comprising a distal end and a proximal end;
 a needle comprising a body terminating in at least one sharp point, the needle being mounted to the distal end of the shaft; and
 a drive shaft movably mounted to the elongated shaft, the drive shaft is adapted to move radially relative to the elongated shaft in order to strike the needle and engage the bone.

In another form of the present invention, there is provided a microfracture instrument for applying microfracture therapy to a bone, the microfracture instrument comprising:
 an elongated shaft comprising a distal end and a proximal end;
 a needle comprising a body terminating in at least one sharp point, the needle being mounted to the distal end of the shaft; and
 a drive shaft movably mounted to the elongated shaft, the drive shaft is adapted to move rotationally relative to the elongated shaft in order to rotate the needle to engage the bone.

In another form of the present invention, there is provided a method for applying microfracture therapy to a bone, the method comprising:
 providing a microfracture instrument comprising:
  an elongated shaft comprising a distal end and a proximal end;

a needle comprising a body terminating in at least one sharp point, the needle being movably mounted to the distal end of the shaft for movement between an extended position for engaging the bone with the at least one sharp point of the needle and a retracted position for withdrawing the at least one sharp point of the needle from the bone; and a drive shaft movably mounted to the elongated shaft, the drive shaft being connected to the body of the needle so that movement of the drive shaft relative to the elongated shaft moves the needle between its extended position and its retracted position;

positioning the elongated shaft adjacent to the bone; and moving the drive shaft so that the sharp point of the needle engages the bone.

In another form of the present invention, there is provided a method for applying microfracture therapy to a bone, the method comprising:

providing a microfracture instrument comprising:

an elongated shaft comprising a distal end and a proximal end;

a needle comprising a body terminating in at least one sharp point, the needle being mounted to the distal end of the shaft; and a drive shaft movably mounted to the elongated shaft, the drive shaft is adapted to move radially relative to the elongated shaft in order to strike the needle and engage the bone;

positioning the elongated shaft adjacent to the bone; and moving the drive shaft so that the sharp point of the needle engages the bone.

In another form of the present invention, there is provided a method for applying microfracture therapy to a bone, the method comprising:

providing a microfracture instrument comprising:

an elongated shaft comprising a distal end and a proximal end;

a needle comprising a body terminating in at least one sharp point, the needle being mounted to the distal end of the shaft; and a drive shaft movably mounted to the elongated shaft, the drive shaft is adapted to move rotationally relative to the elongated shaft in order to rotate the needle to engage the bone;

positioning the elongated shaft adjacent to the bone; and moving the drive shaft so that the sharp point of the needle engages the bone.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIGS. 19-21 are schematic views showing a fourth microfracture instrument formed in accordance with the present invention;

DETAILED DESCRIPTION OF THE PREFERRED EMBODIMENTS

Figure 1:
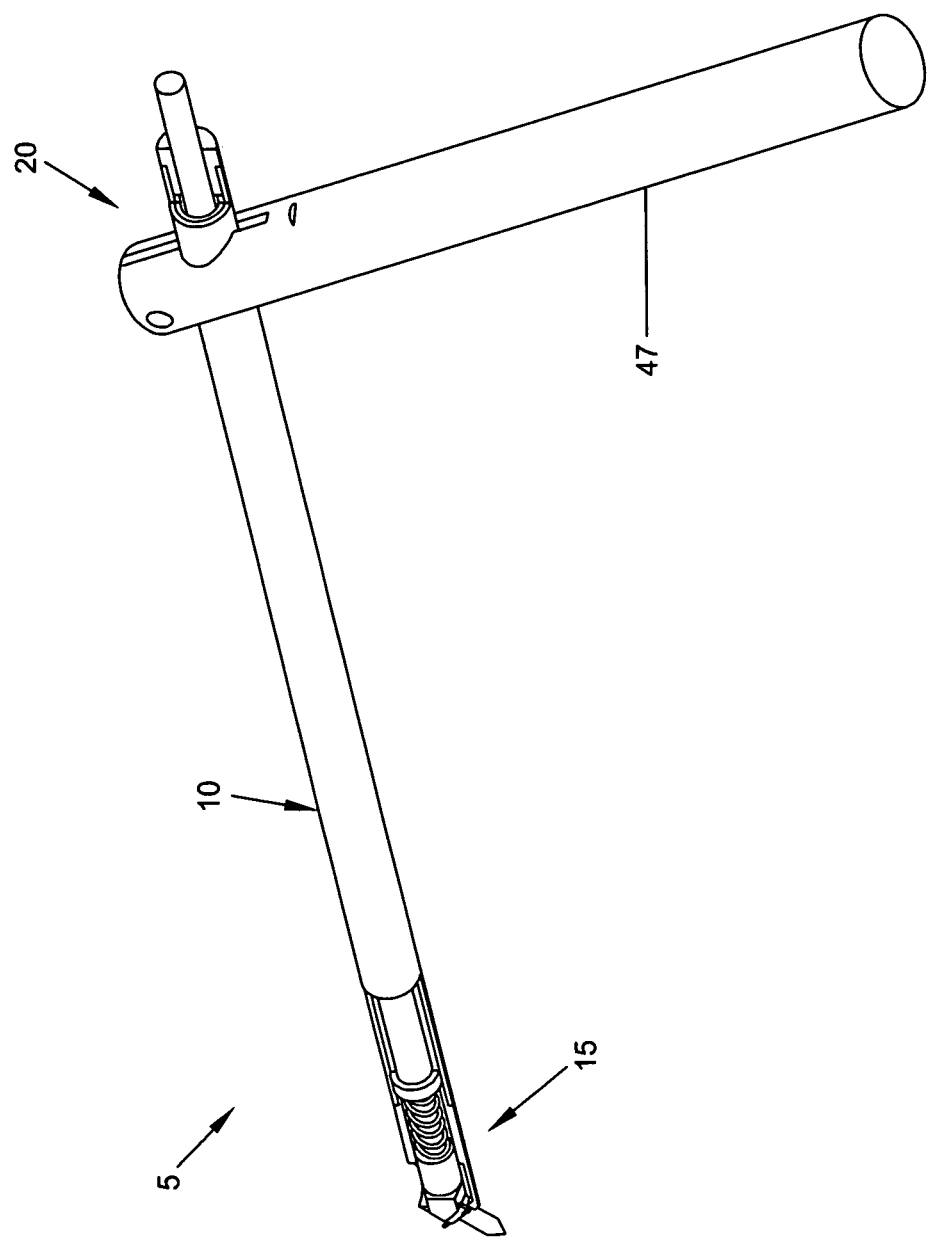
FIGS. 1-10 are schematic views showing a first microfracture instrument formed in accordance with the present invention.
Figure 2:
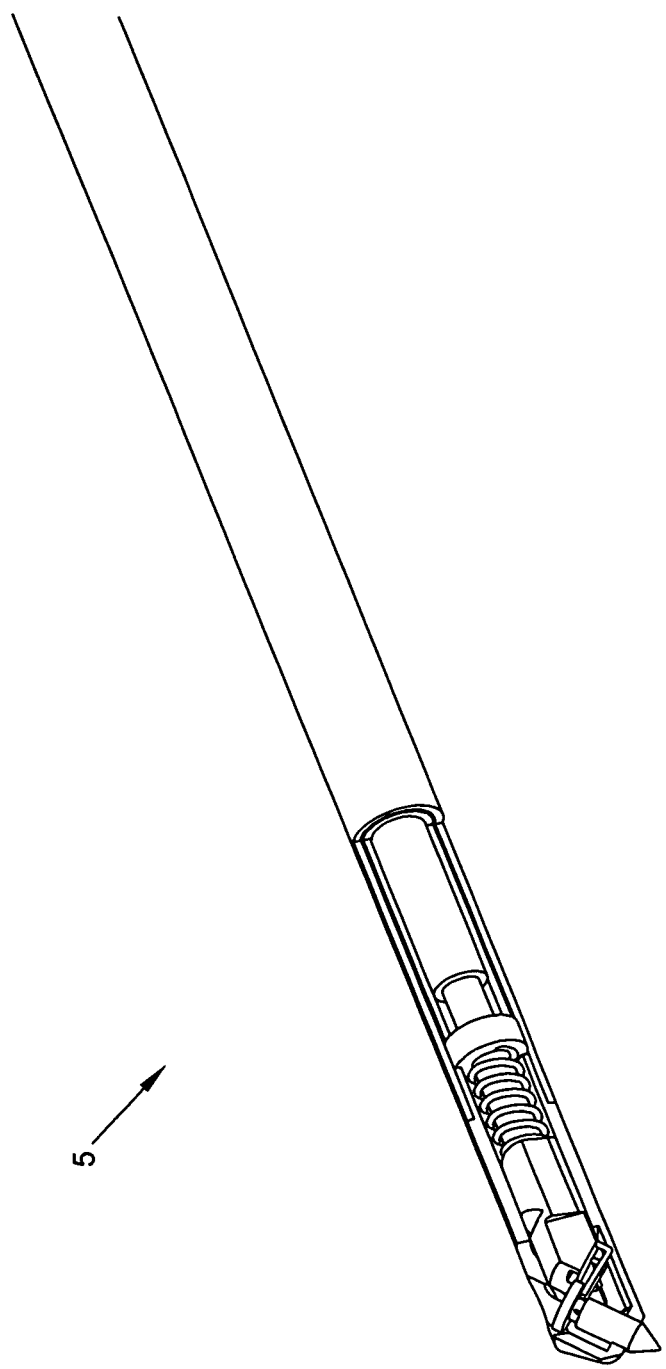
Figure 3:
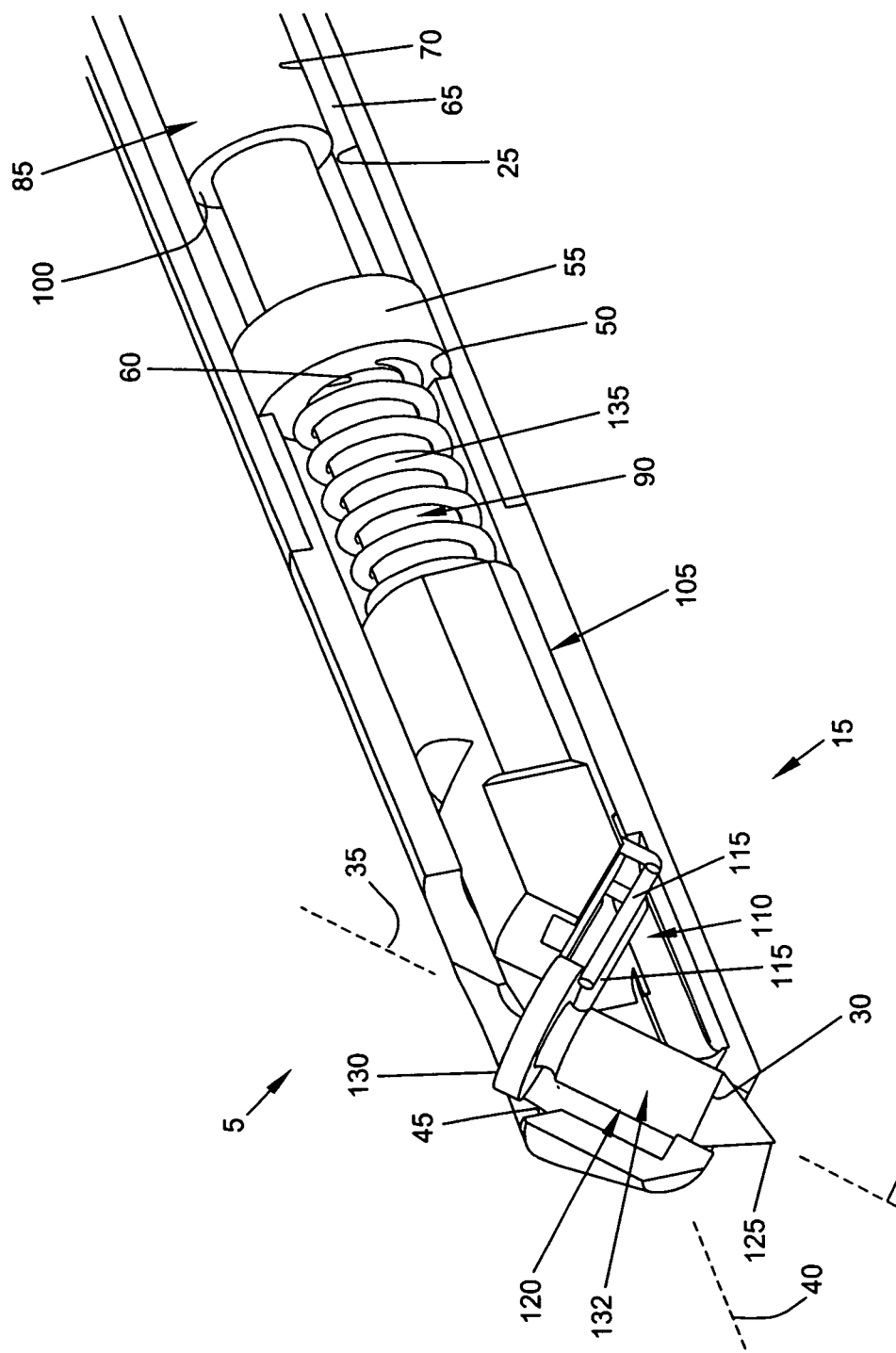
Figure 4:
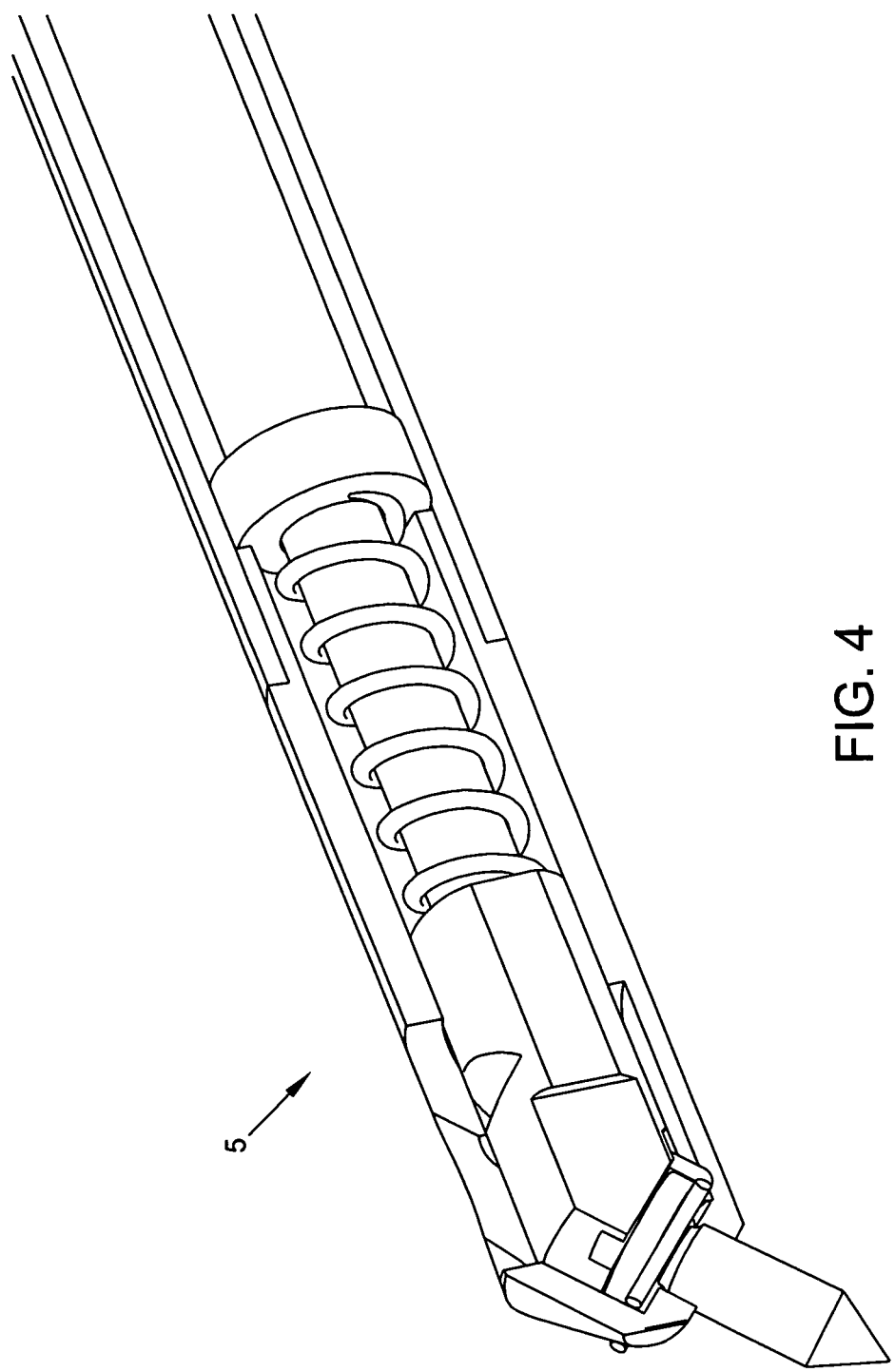
Figure 5:
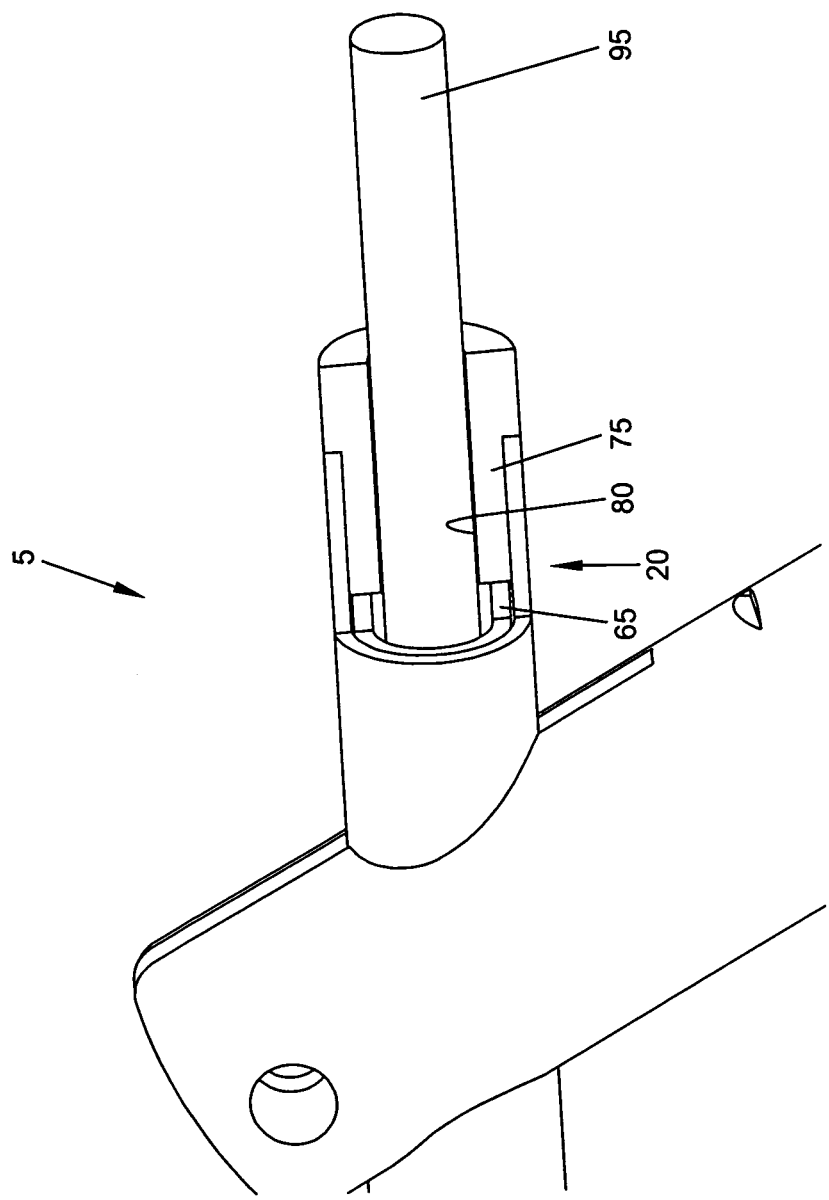
Figure 6:
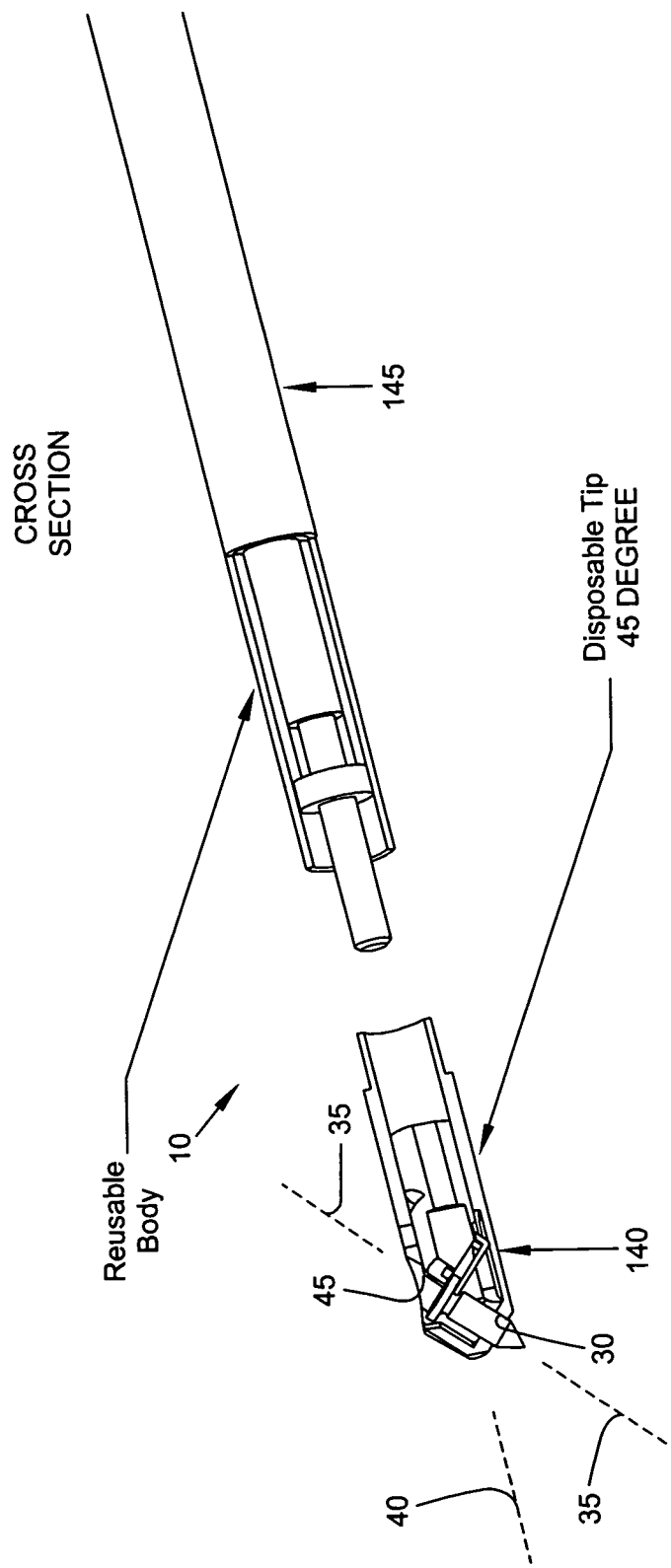
Figure 7:
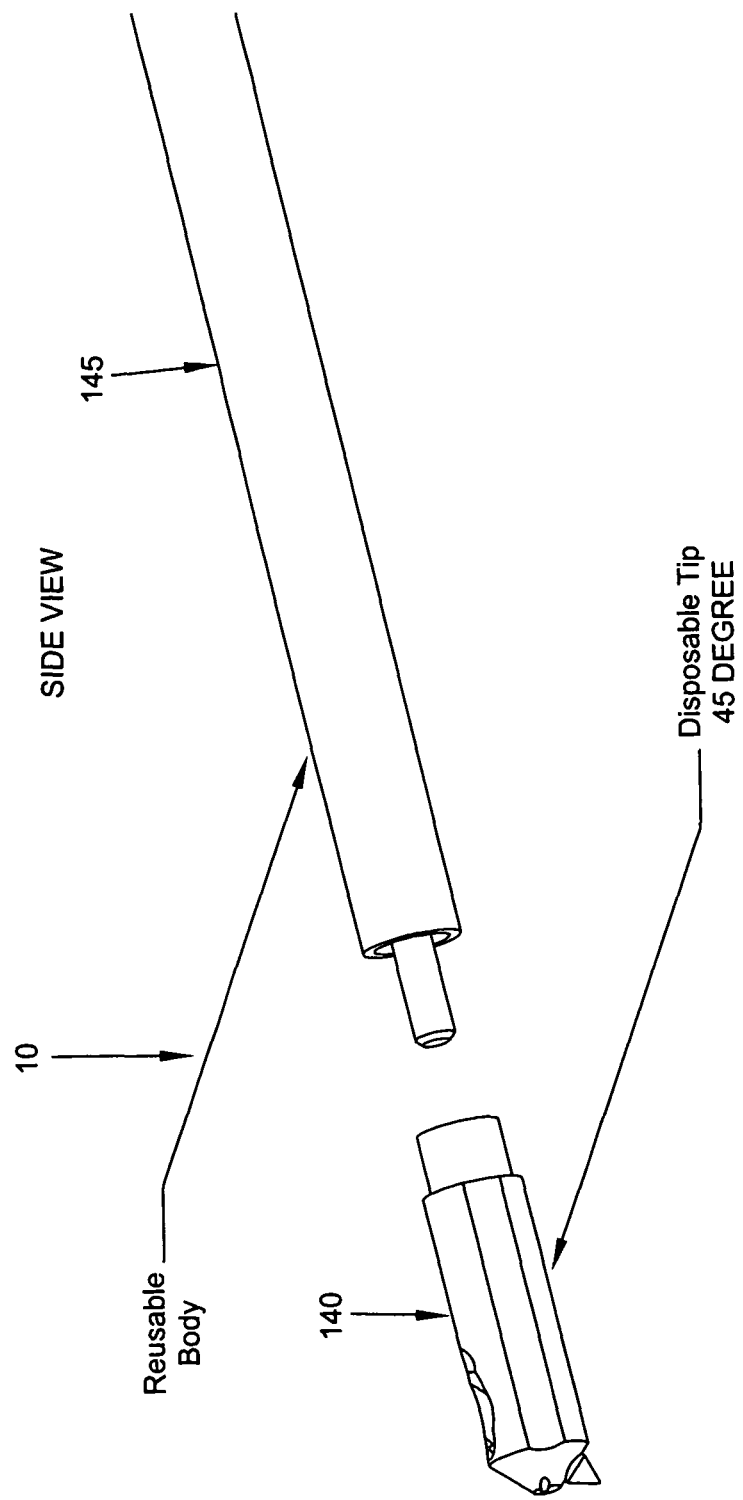
Figure 8:
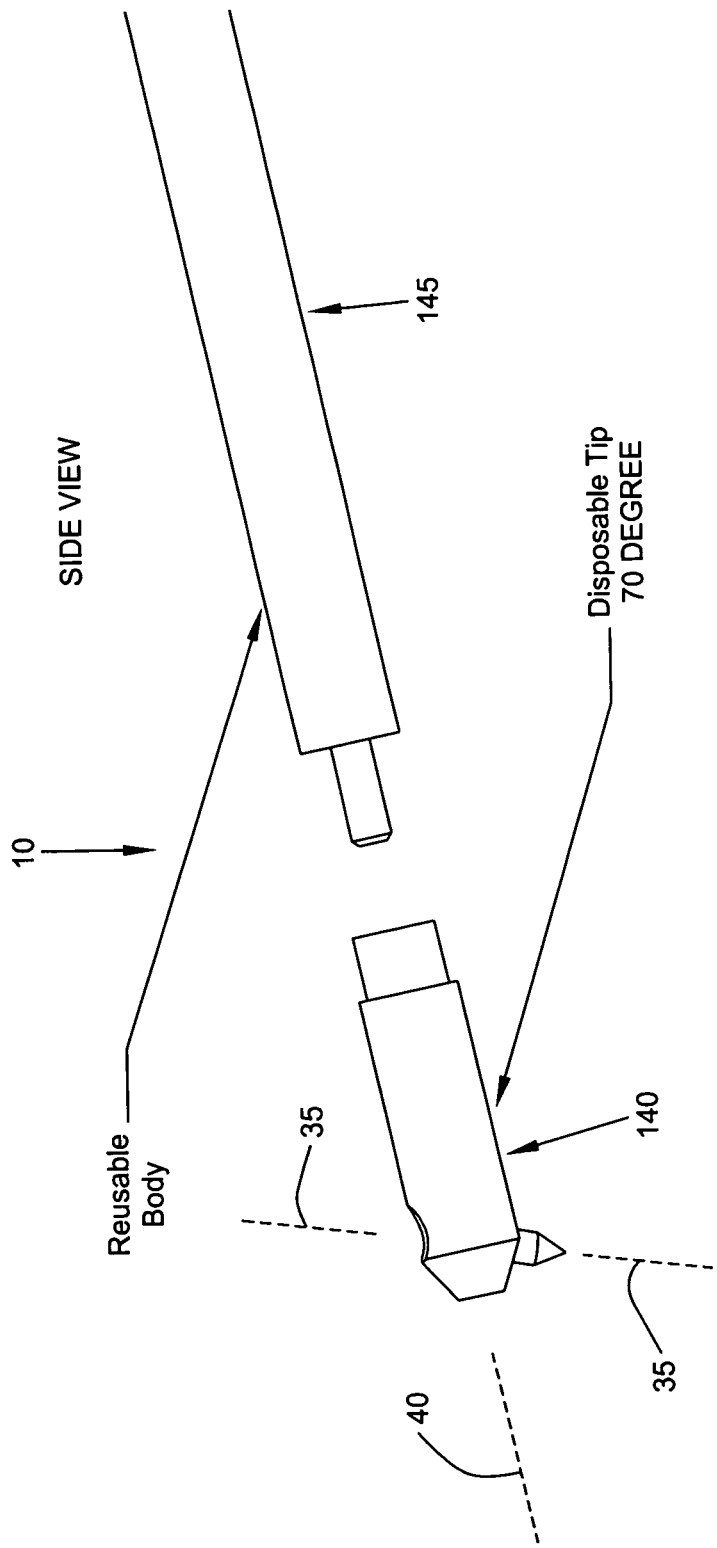

The present invention comprises the provision and use of novel apparatus for performing arthroscopic microfracture surgery. The novel apparatus permits the microfracture therapy to be applied to a bone surface even where that bone surface is set at an angle to the axis of approach and/or where it might otherwise be difficult or impossible to use a conventional pick or awl to perform the microfracture surgery.

More particularly, and looking now at FIGS. 1-5, there is shown a novel microfracture instrument 5 formed in accordance with the present invention.

Microfracture instrument 5 generally comprises a hollow shaft 10 (FIG. 1) having a distal end 15, a proximal end 20, and a lumen 25 (FIG. 3) extending therebetween. Distal end 15 of hollow shaft 10 has an opening 30 (FIG. 3) formed therein. The longitudinal axis 35 of opening 30 is set at an acute angle to the longitudinal axis 40 of hollow shaft 10. Preferably, distal end 15 of hollow shaft 10 also has an opening 45 formed therein. Preferably opening 45 is aligned with opening 30 along longitudinal axis 35. A handle 47 (FIG. 1) is secured to hollow shaft 10 near the proximal end of the shaft.

A shoulder 50 is formed on the inside wall of hollow shaft 10, proximal to openings 30 and 45. A stop 55, having a central opening 60 formed therein, is disposed within lumen 25 so that the stop engages shoulder 50. A spacer tube 65, having a lumen 70 extending therethrough, is disposed within lumen 25 of hollow shaft 10 so as to capture stop 55 against shoulder 50. An end cap 75 (FIG. 5), having a lumen 80 extending therethrough, captures spacer tube 65 within lumen 25.

A drive shaft 85 is movably disposed within hollow shaft 10. More particularly, drive shaft 85 comprises a distal end 90 having a diameter sized to be slidably received within central opening 60 in stop 55, and a proximal end 95 sized to be slidably received within spacer tube 65 and end cap 75. An annular shoulder 100 is disposed intermediate drive shaft 85. Annular shoulder 100 engages stop 55 so as to limit distal movement of drive shaft 85. See FIGS. 3 and 4.

A drive head 105 is disposed on the distal end of drive shaft 85. A bifurcated seat 110 is disposed on the distal end of drive head 105. More particularly, bifurcated seat 110 comprises a pair of spaced arms 115 which are disposed at a right angle to the longitudinal axis 35 of opening 30. A needle 120, terminating in a sharp distal tip 125 and a proximal flanged head 130, is slidably mounted in bifurcated seat 110, with the shank 132 of needle 120 received between spaced arms 115. As a result of this construction, proximal and distal movement of drive shaft 85 along longitudinal axis 40 causes needle 120 to be retracted into, or projected out of, opening 30 of hollow shaft 10 along longitudinal axis 35. Thus, microfracture instrument 5 can be advanced to a surgical site along longitudinal axis 40, yet deliver its needle 120 for microfracture therapy along a different longitudinal axis 35. This is a significant improvement over the prior art.

A spring 135 is disposed between drive head 105 and stop 55.

In one form of the invention, spring 135 is a tension spring, so that drive shaft 85 is normally biased proximally within hollow shaft 10, and so that needle 120 normally has its sharp distal point 125 in its retracted position wherein the sharp distal point 125 lies within an axial projection of the outer perimeter of hollow shaft 10. See FIG. 3. However, the proximal end of drive shaft 85 may be moved distally (e.g., by tapping it with a hammer or mallet) so that needle 120 has its sharp distal point 125 in its projected position wherein the sharp distal point 125 projects beyond an axial projection of the outer perimeter of hollow shaft 10. See FIG. 4. In this way, needle 120 can be used to score a bone in a microfracture procedure. Thus, with this form of the invention, microfracture instrument 5 may be advanced to the surgical site along longitudinal axis 40 with the sharp distal point of needle 120 safely retracted inboard of the instrument, and then the proximal end of drive shaft 85 struck with a hammer or mallet so as to drive the sharp distal point of needle 120 along longitudinal axis 35 so as to deliver microfracture therapy to a bone.

In another form of the invention, spring 135 is a compression spring, so that drive shaft 85 is normally biased distally within hollow shaft 10, and so that needle 120 normally has its sharp distal point 125 in its projected position wherein the sharp distal point 125 projects beyond an axial projection of the outer perimeter of hollow shaft 10. See FIG. 4. However, the proximal end of drive shaft 85 may be moved proximally (e.g., by gripping it manually and pulling it proximally) so that needle 120 has its sharp distal point 125 in its retracted position wherein the sharp distal point 125 lies within an axial projection of the outer perimeter of hollow shaft 10. See FIG. 3. Thereafter, when a bone is to be scored, the proximal end of drive shaft 85 is released, causing compression spring 125 to drive needle 120 out of the distal end of hollow shaft 10 and into the bone. Alternatively, the proximal end of drive shaft 85 can be released, so that needle 120 projects out of hollow shaft 10 so that the surgeon can position it on the bone, and then the proximal end of the drive shaft 85 struck (e.g., with a hammer or mallet) so as to drive sharp distal point 125 into bone. Thus, with this form of the invention, microfracture instrument 5 may have its drive shaft 85 pulled proximally by hand and then the instrument advanced to the surgical site along longitudinal axis 40 with the sharp distal point of needle 120 safely retracted inboard of the instrument, and then the proximal end of drive shaft 85 may be released (and/or struck with a hammer or mallet) so as to drive the sharp distal point of needle 120 along its longitudinal axis 35 so as to deliver microfracture therapy to a bone.

Figure 9:
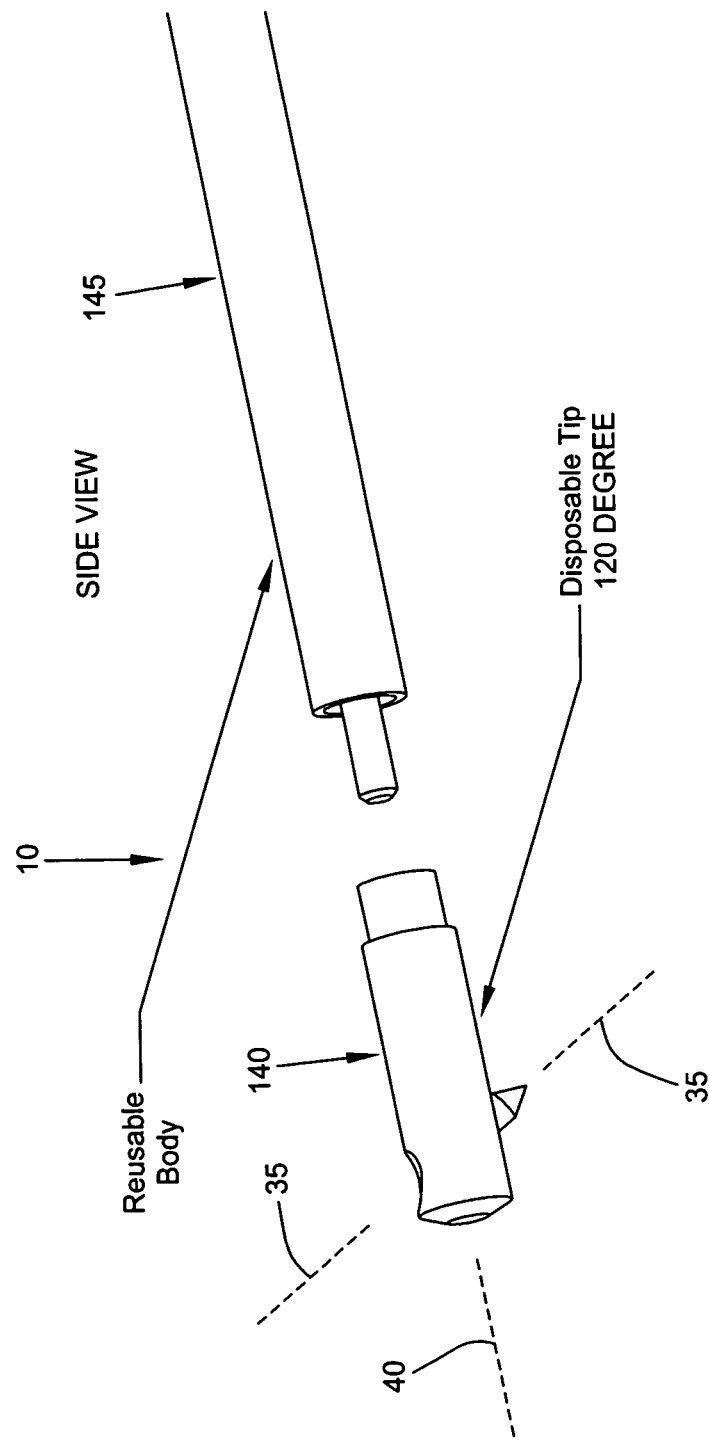
Figure 10:
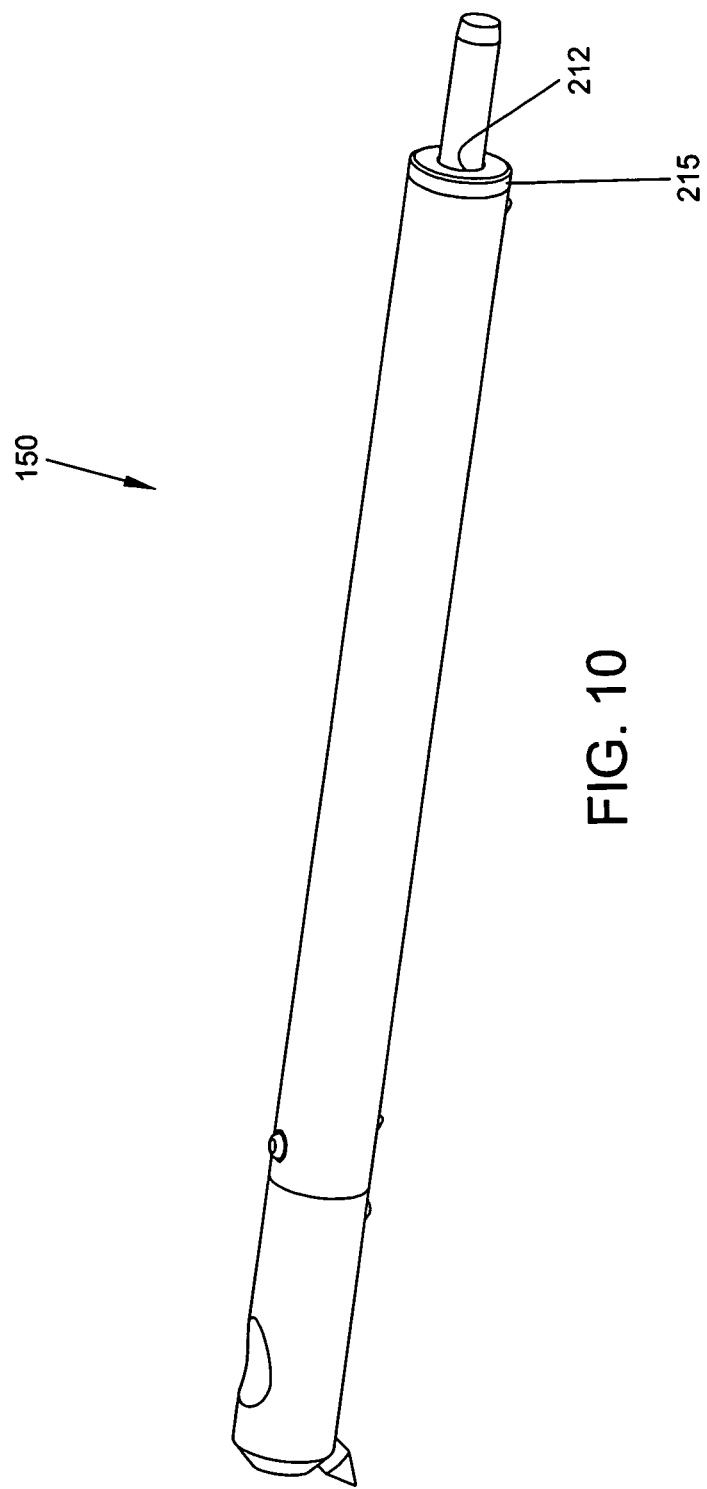
Figure 11:
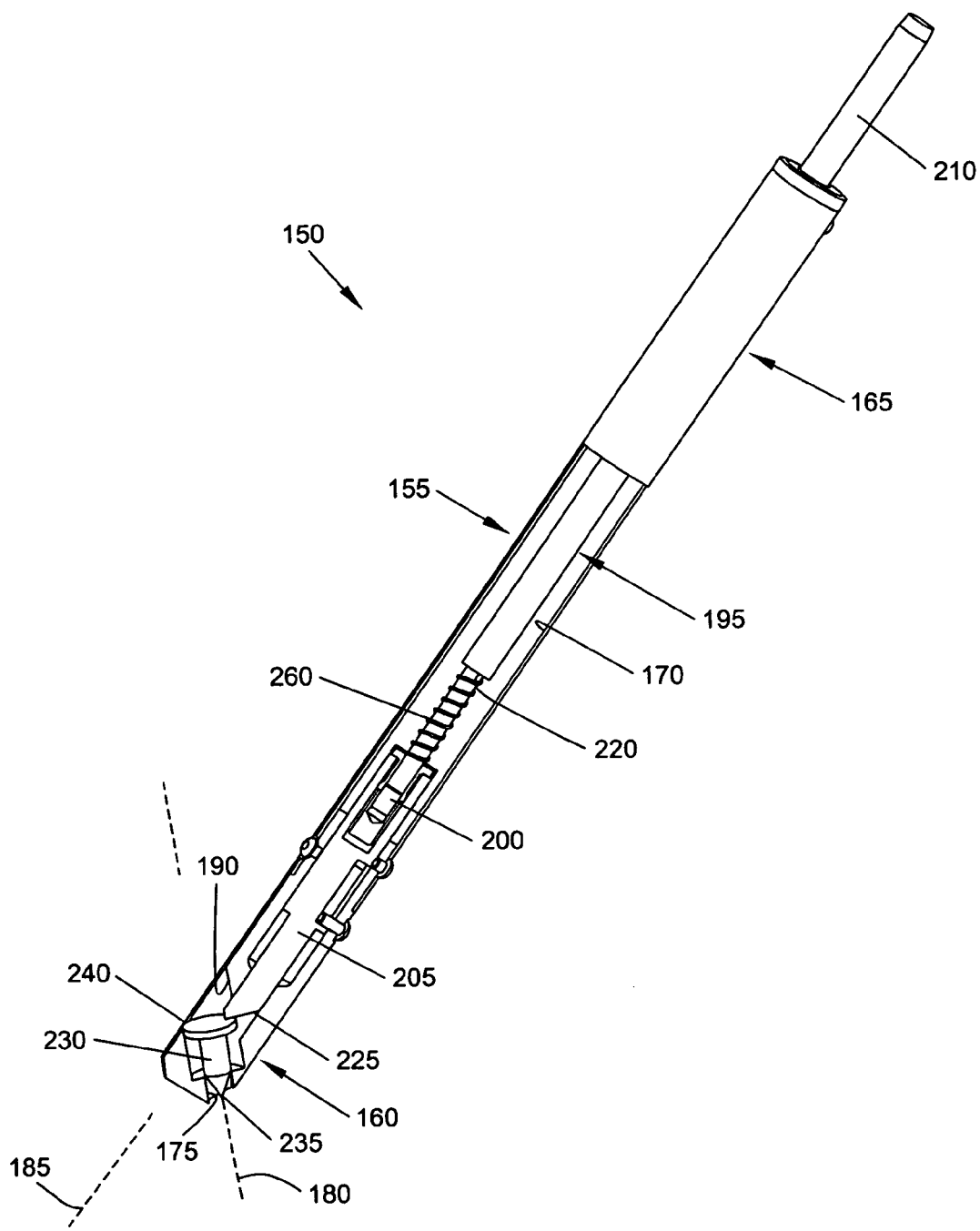
FIGS. 11-15 are schematic views showing a second microfracture instrument formed in accordance with the present invention.
Figure 12:
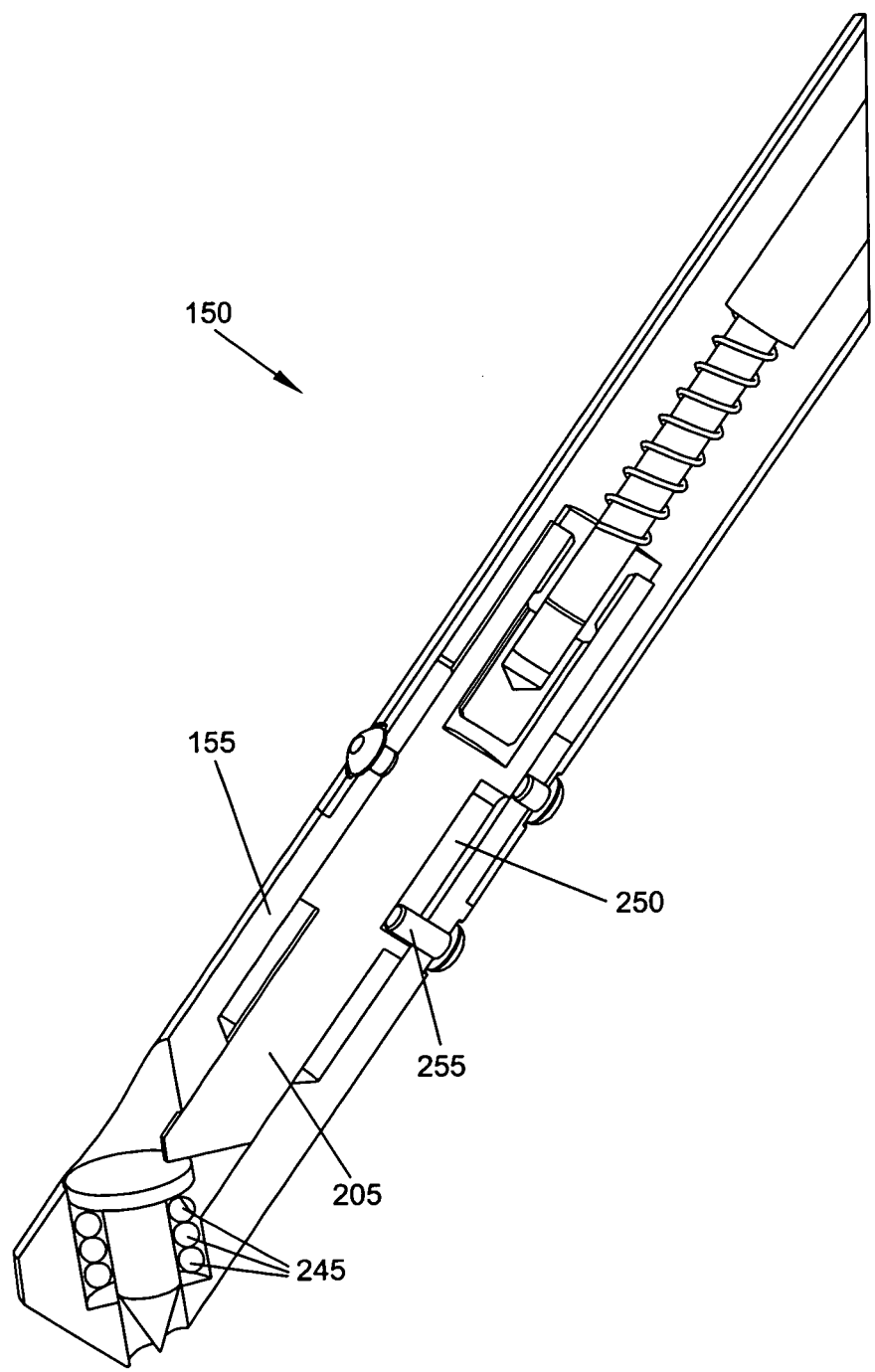
Figure 13:
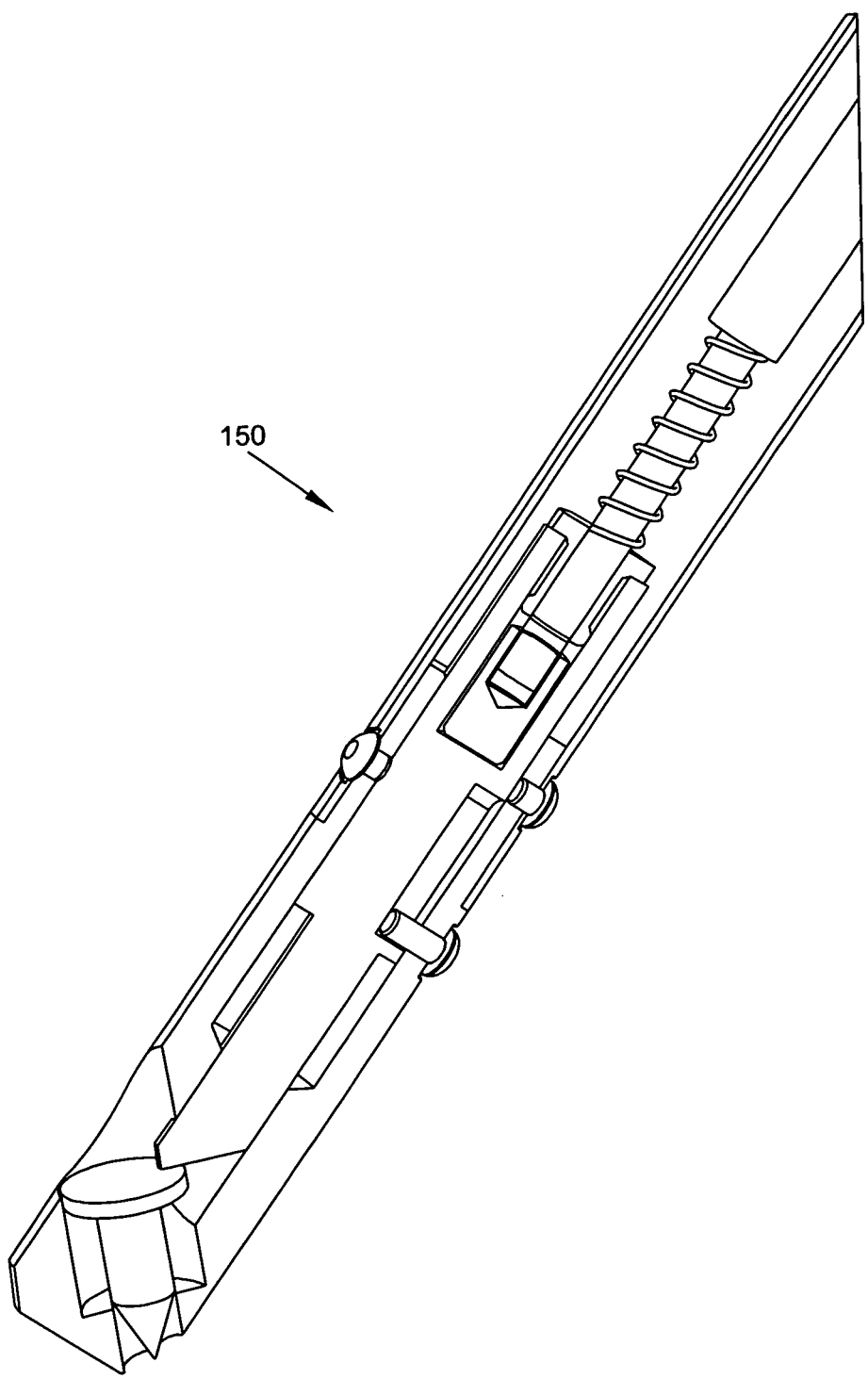
Figure 14:
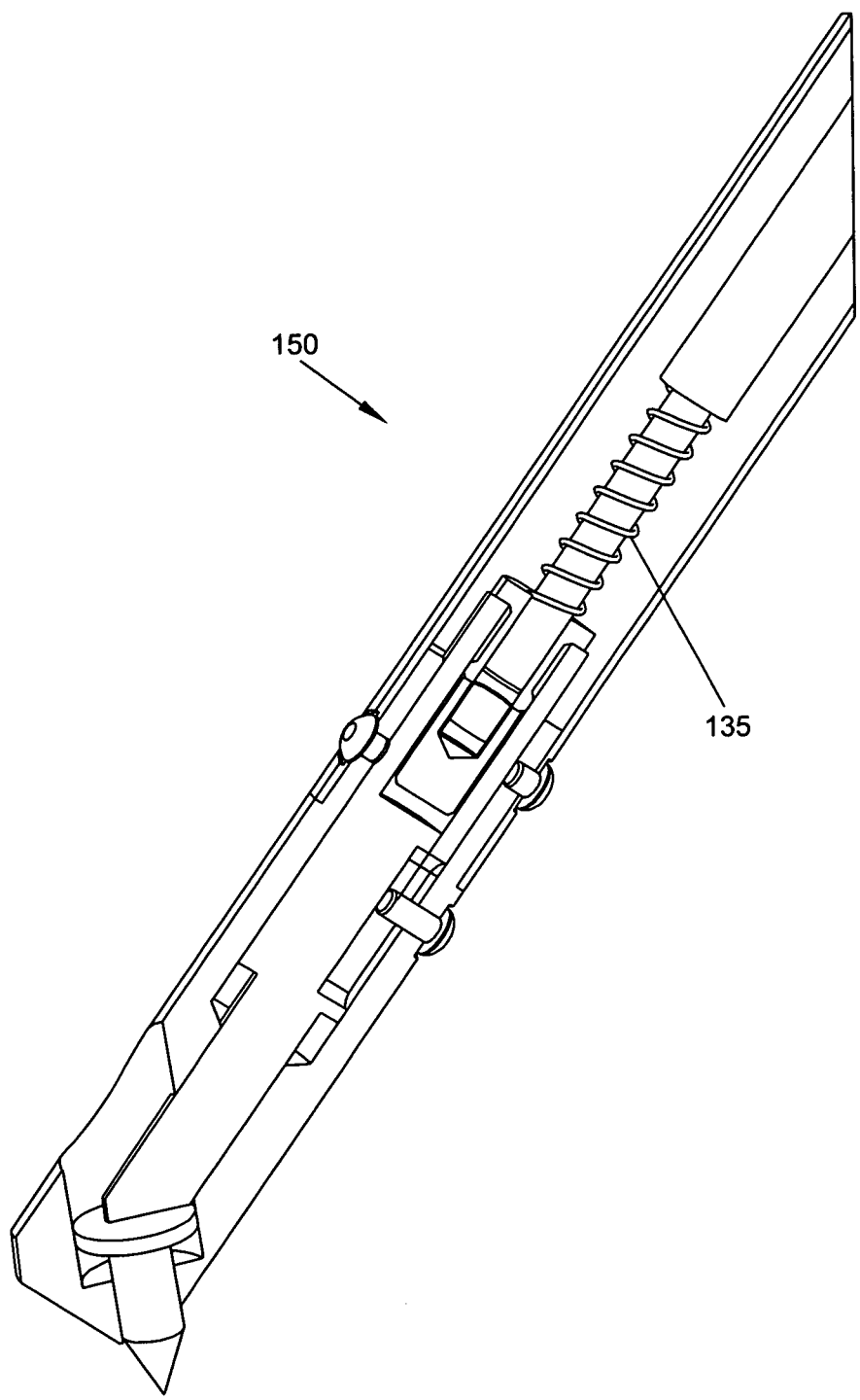
Figure 15:
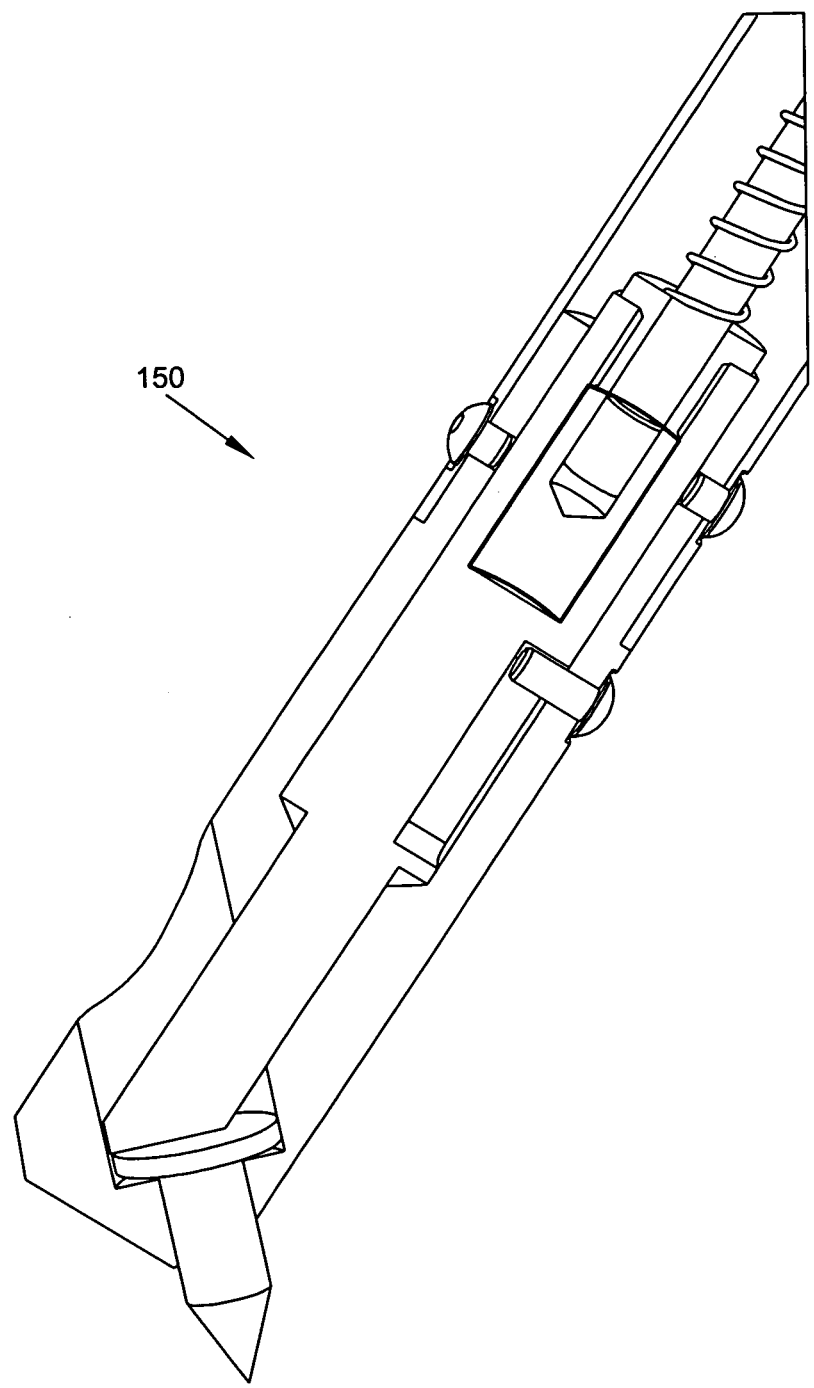

As seen in FIGS. 1-4 and 6-9, hollow shaft 10 can be formed with a modular construction so that different distal tip configurations can be accommodated. More particularly, in this form of the invention, hollow shaft 10 can comprise a distal segment 140 which selectively attaches to a proximal segment 145. Distal segment 140 can have its openings 30 and 45 set at various angles relative to the longitudinal axis of hollow shaft 10 so as to accommodate a range of surgical applications. In other words, longitudinal axis 35 of openings 30 and 45 can be set at various angles (e.g., 30°, 60°, etc.) to the longitudinal axis 40 of hollow shaft 10. In some embodiments, the angle is greater than 90°, as shown in FIG. 9. In this situation, the drive shaft may be pulled in the proximal direction to drive the needle into the bone. The proximal portion of the device is the same, except that it is configured to drive the needle in a retrograde fashion, and the reusable portion is designed for the desired retrograde angle. Furthermore, if desired, distal segment 140 can be made disposable and proximal segment 145 can be made reusable.

Looking next at FIGS. 10-15, there is shown another novel microfracture instrument 150 formed in accordance with the present invention. Microfracture instrument 150 is similar to the novel microfracture instrument 5 discussed above, except as will hereinafter be discussed in further detail. More particularly, novel microfracture instrument 150 generally comprises a hollow shaft 155 (FIG. 11) having a distal end 160, a proximal end 165, and a lumen 170 extending therebetween. Distal end 160 of hollow shaft 155 has an opening 175 formed therein. The longitudinal axis 180 of opening 175 is set at an acute angle to the longitudinal axis 185 of hollow shaft 170. Preferably, distal end 165 of hollow shaft 155 also has an opening 190 formed therein. Preferably opening 190 is aligned with opening 175 along longitudinal axis 180.

A drive shaft 195 is movably disposed within hollow shaft 155. Drive shaft 195 comprises a distal end 200 having a diameter sized to be secured to a drive head 205, and a proximal end 210 sized to be slidably received within an opening 212 (FIG. 10) formed in an end cap 215. An annular shoulder 220 (FIG. 11) is disposed intermediate drive shaft 195.

Drive head 205 is disposed on the distal end of drive shaft 195. An angled surface 225 is disposed at a right angle to the longitudinal axis 180 of opening 175. A needle 230, terminating in a sharp distal tip 235 and a proximal flanged head 240, is slidably mounted in openings 175 and 190. A spring 245 (FIG. 12) biases needle 230 in its retracted position, wherein the sharp distal point 235 of needle 230 lies within an axial projection of the outer perimeter of hollow shaft 155. As a result of this construction, proximal and distal movement of drive shaft 195 along longitudinal axis 185 causes needle 230 to be retracted into, or projected out of, opening 175 of hollow shaft 155 along longitudinal axis 180. Thus, microfracture instrument 150 can be advanced to a surgical site along longitudinal axis 185, yet deliver its needle 230 for microfracture therapy along a different longitudinal axis 180. This is a significant improvement over the prior art.

A slot 250 (FIG. 12) formed in drive head 205 cooperates with a pin 255 set in hollow shaft 155 so as to limit distal and proximal movement of drive shaft 195. See FIGS. 12 and 15.

A spring 260 is disposed between drive head 205 and shoulder 220. Spring 260 pushes drive shaft 195 and drive head 205 away from each other, yet allows them to move relative to one another. Spring 260 creates tension between the said parts for the purpose of multiplying the strength of the "tap" coming from drive shaft 195 when applied onto drive head 205. Components 260, 195 and 205 move together in direction from proximal end to distal end with each "tap" applied on shaft 210.

In one form of the invention, spring 260 is a tension spring, so that drive shaft 195 is normally biased proximally within hollow shaft 155, and so that needle 230 normally has its sharp distal point 235 in its retracted position wherein the sharp distal point 235 lies within an axial projection of the outer perimeter of hollow shaft 155. See FIG. 11. However, the proximal end of drive shaft 195 may be moved distally (e.g., by tapping it with a hammer or mallet) so that needle 230 has its sharp distal point 235 in its projected position wherein the sharp distal point 235 projects beyond an axial projection of the outer perimeter of hollow shaft 155. See FIG. 15. In this way, needle 230 can be used to score a bone in a microfracture procedure. Thus, with this form of the invention, microfracture instrument 150 may be advanced to the surgical site along longitudinal axis 185 with the sharp distal point of needle 230 safely retracted inboard of the instrument, and then the proximal end of drive shaft 195 struck with a hammer or mallet so as to drive the sharp distal point of needle 230 along its longitudinal axis 180 so as to deliver microfracture therapy to a bone.

In another form of the invention, spring 260 is a compression spring, so that drive shaft 195 is normally biased distally within hollow shaft 155, and so that needle 230 normally has its sharp distal point 235 in its projected position wherein the sharp distal point projects beyond an axial projection of the outer perimeter of hollow shaft 155. See FIG. 15. However, the proximal end of drive shaft 195 may be moved proximally (e.g., by gripping it manually and pulling it proximally) so that needle 230 has its sharp distal point 235 in its retracted position wherein the sharp distal point 235 lies within an axial projection of the outer perimeter of hollow shaft 155. See FIG. 11. Thereafter, when a bone is to be scored, the proximal end of drive shaft 195 is released, causing compression spring 260 to drive needle 230 out of the distal end of hollow shaft 155 and into the bone. Alternatively, the proximal end of drive shaft 195 can be released, so that needle 230 projects out of hollow shaft 155 so that the surgeon can position it on the bone, and then the proximal end of the drive shaft 195 struck (e.g., with a hammer or mallet) so as to drive sharp distal point 235 into bone. Thus, with this form of the invention, microfracture instrument 5 may have its drive shaft 195 pulled proximally by hand and then the instrument advanced to the surgical site along longitudinal axis 185 with the sharp distal point of needle 230 safely retracted inboard of the instrument, and then the proximal end of drive shaft 195 may be released (and/or struck with a hammer or mallet) so as to drive the sharp distal point of needle 230 along its longitudinal axis 180 so as to deliver microfracture therapy to a bone.

Figure 16:
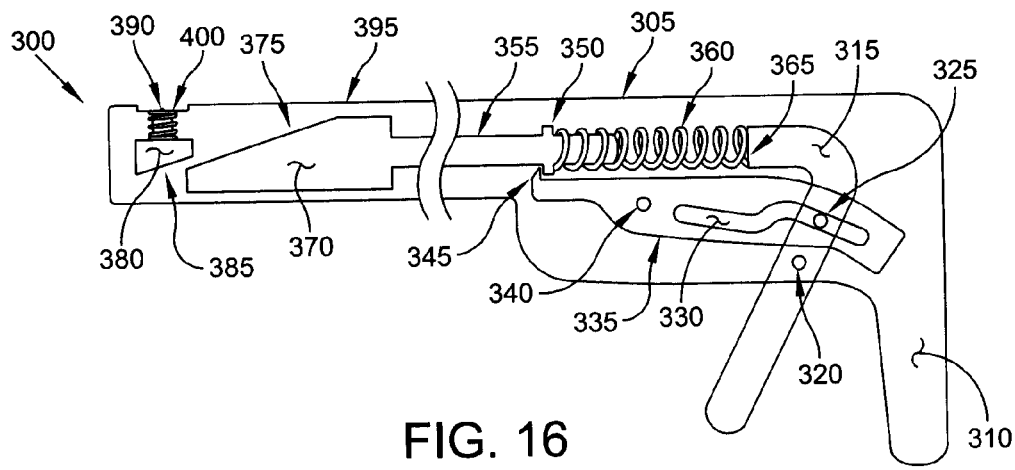
FIGS. 16-18 are schematic views showing a third microfracture instrument formed in accordance with the present invention.
Figure 17:
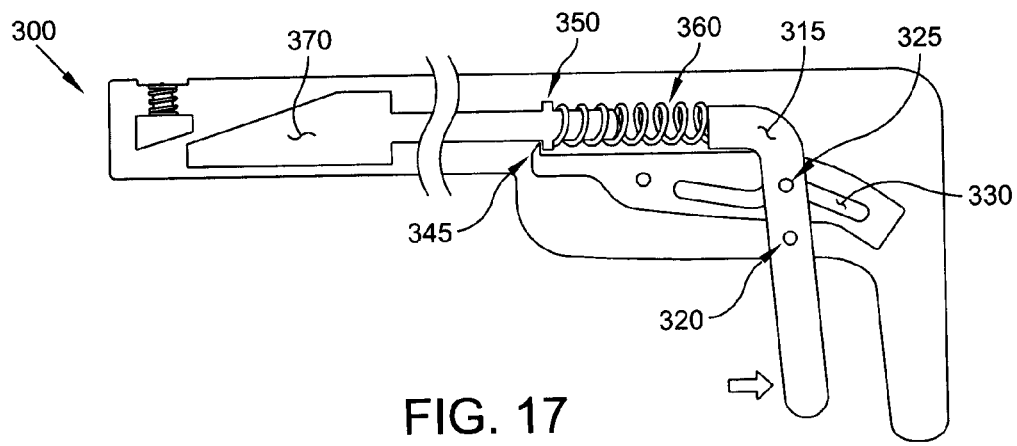
Figure 18:
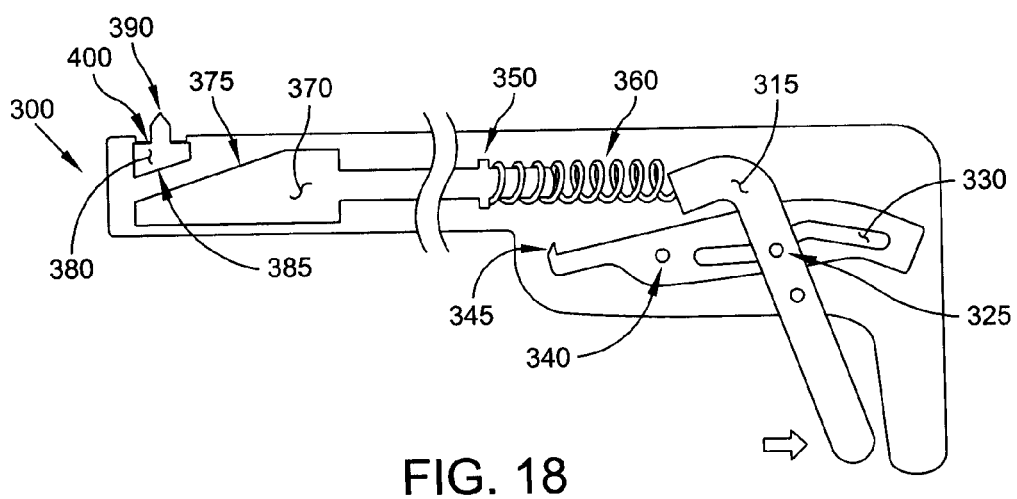

Looking next at FIGS. 16-18, there is shown another novel microfracture instrument 300 formed in accordance with the present invention. This construction provides an alternative approach for creating a large amount of potential energy and then suddenly releasing that potential energy to a sharp tip in order to create a small defect in bone for a microfracture procedure.

Microfracture instrument 300 comprises a housing 305 which includes a palm area 310 and a trigger 315. Trigger 315 pivots at a pin 320 and includes a guide pin 325 which rides in a guide rail 330 of a pawl 335. Pawl 335 rotates about a pawl pin 340 so a lock tab 345 rests against a shoulder 350 of a drive shaft 355. Trigger 315 is also attached to a spring 360 at connection 365. Spring 360 is also attached to shaft 355 proximal of shoulder 350. The distal end of drive shaft 355 is configured as a block 370 with a wedge surface 375. Wedge surface 375 is in contact with a needle or punch 380 at a punch wedge surface 385. The punch tip 390 is held in the outer tube 395 of housing 305 by a punch spring 400.

In use, and looking now at FIG. 17, trigger 315 is actuated so that it pivots on pin 320 and guide pin 325 rides along guide rail 330. However, pawl 335 does not move at this time, because the radius of movement of guide pin 325 is the same as the radius of guide rail 330 over this span. Since trigger 315 is moving, spring 360 begins to compress against shoulder 350. Shoulder 350 does not move because lock tab 345 holds it in place.

In FIG. 18, trigger 315 is actuated a little further such that guide pin 325 starts to run on a steep part of guide rail 330, which forces pawl 335 to rotate about pawl pin 340. This motion lowers lock tab 345 away from shoulder 350, such that shaft 355 is allowed to move distally quickly, based on the potential energy of compressed spring 360. With this action, block 370 and its wedge surface 375 also move distal. Wedge surface 375 slides against punch wedge 385, pushing it against spring 400. As a result, punch 380 (and punch tip 390) shoots out of outer tube 395 and into the adjacent tissue (not shown) so as to apply microfracture therapy to the bone.

When trigger 315 is released, spring 360 is pulled proximally at connection point 365, which pulls shaft 355 and block 370 allowing the punch 380 to drop back in to the outer tube 395 with the help of the punch spring 400.

Looking next at FIGS. 19-21, there is shown another microfracture instrument 400 formed in accordance with the present invention. Microfracture instrument 400 generally comprises an elongated shaft 405 having, at its distal end, a first flexible extension 410 and a second flexible extension 415. First flexible extension 410 comprises a needle 420 having a sharp tip 425 thereon.

As a result of this construction, when second flexible extension 415 is pulled away from first flexible extension 410 (e.g., by pulling on a cable 430) and then released, second flexible extension 415 will drive against first flexible extension 415 so as to drive sharp tip 425 of needle 420 against a bone 435, whereby to provide microfracture therapy.

Figure 22:
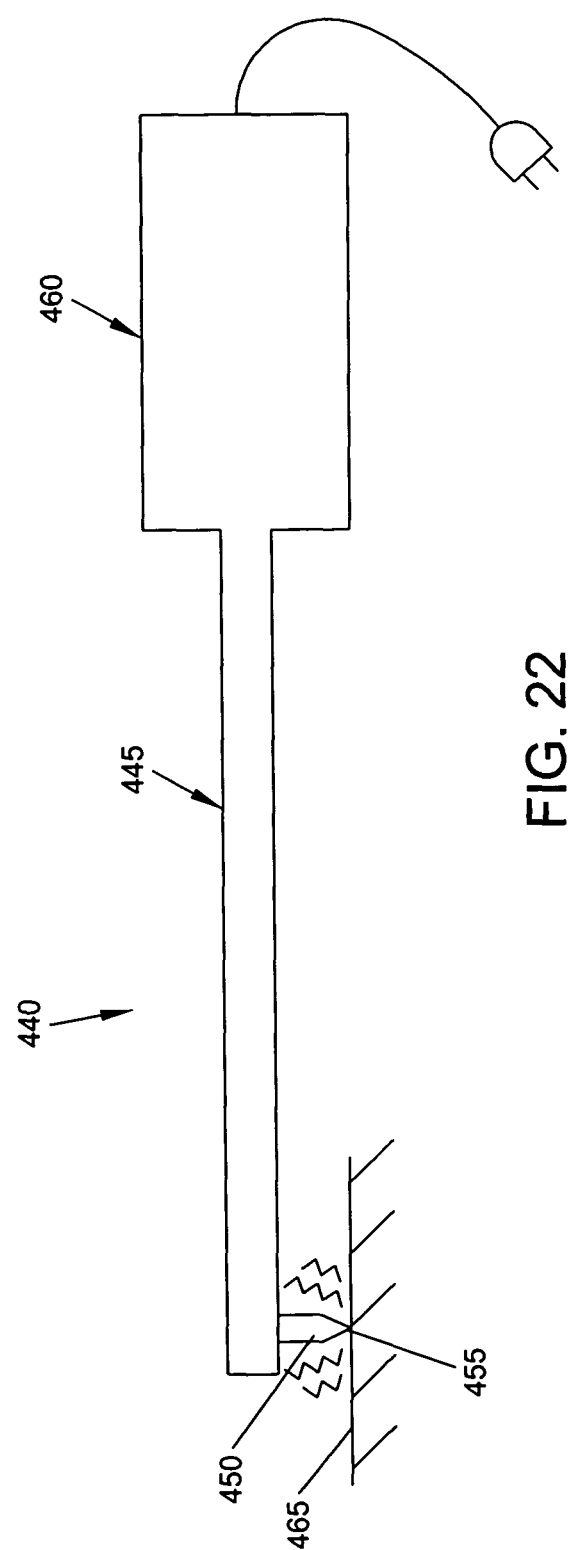
FIG. 22 is a schematic view showing a fifth microfracture instrument formed in accordance with the present invention.

Looking next at FIG. 22, there is shown another microfracture instrument 440 formed in accordance with the present invention. Microfracture instrument 440 generally comprises an elongated shaft 445. At the distal end of elongated shaft 445 is a needle 450 having a sharp tip 455 thereon. The proximal end of elongated shaft 445 is connected to a powered driver 460. Powered driver 460 is adapted to move shaft 445 so that needle 450 moves towards and away from bone 465. By way of example but not limitation, powered driver 460 may comprise an electrical or pneumatic oscillator. An electrical oscillator, for example, may use an ultrasonic frequency.

As a result of this construction, when needle 450 is positioned against bone 465 and powered driver 460 activated, sharp tip 455 of needle 450 is driven against bone 465, whereby to provide microfracture therapy.

Figure 23:
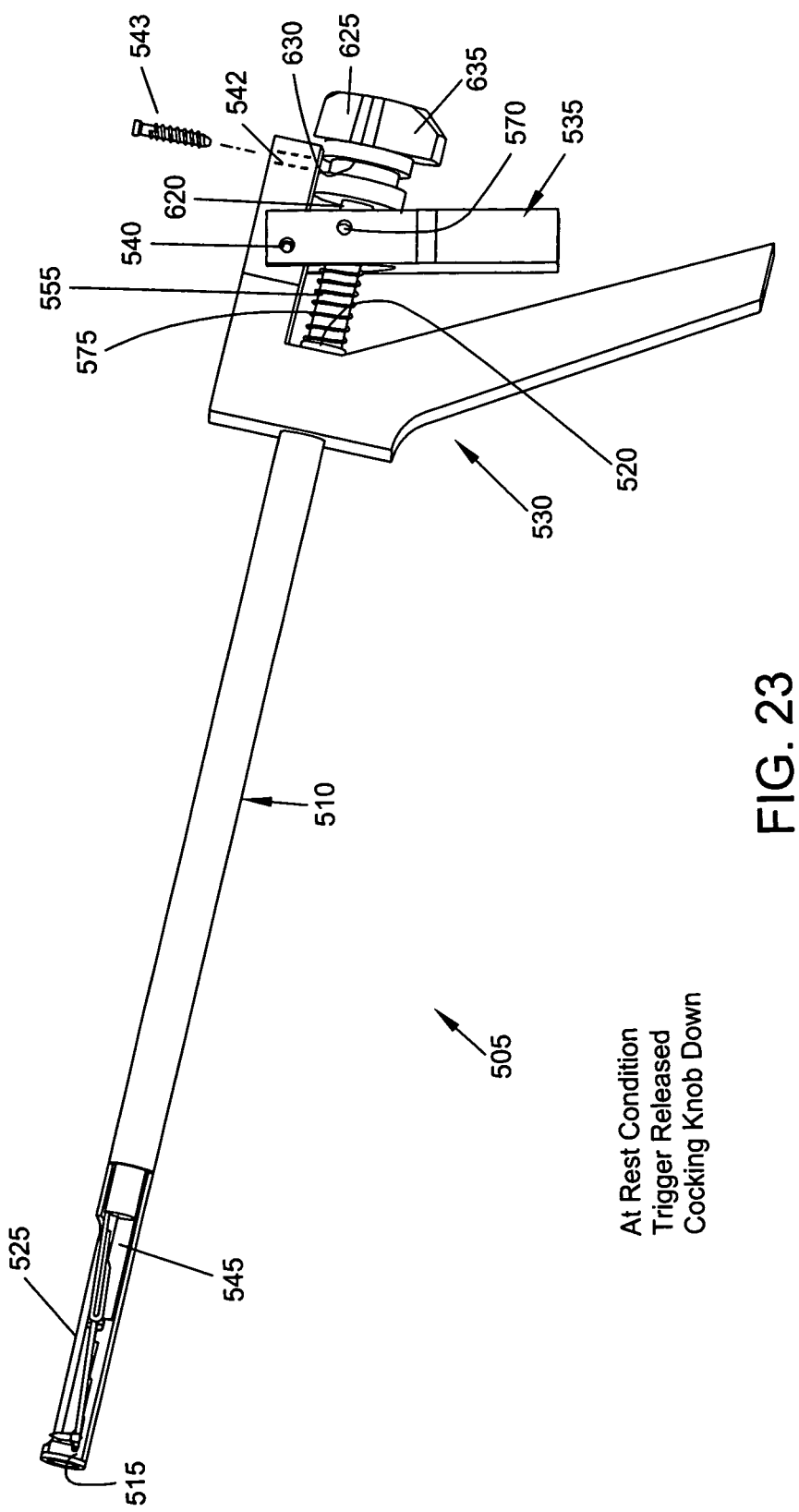
FIGS. 23-34 are schematic views showing a sixth microfracture instrument formed in accordance with the present invention.
Figure 24:
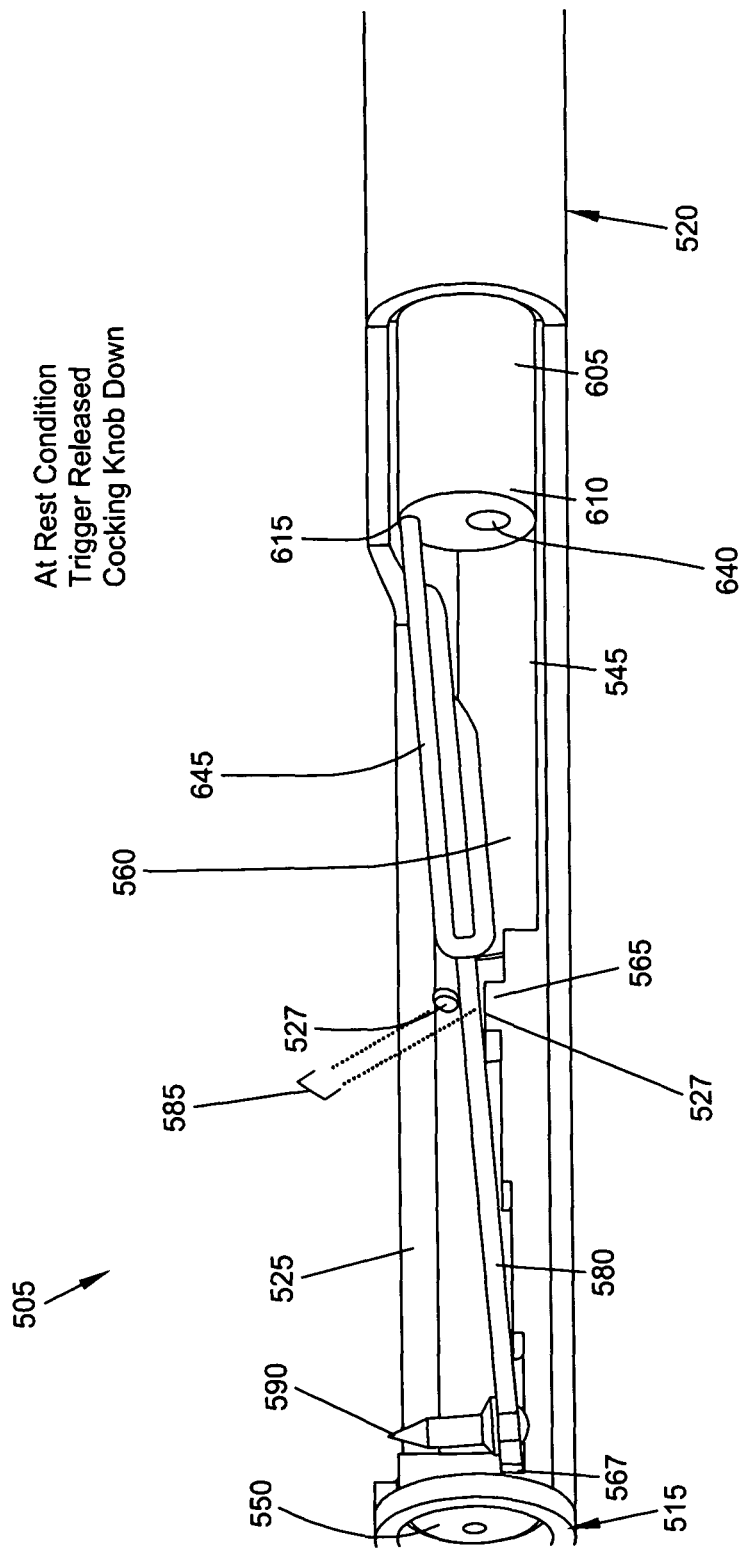
Figure 25:
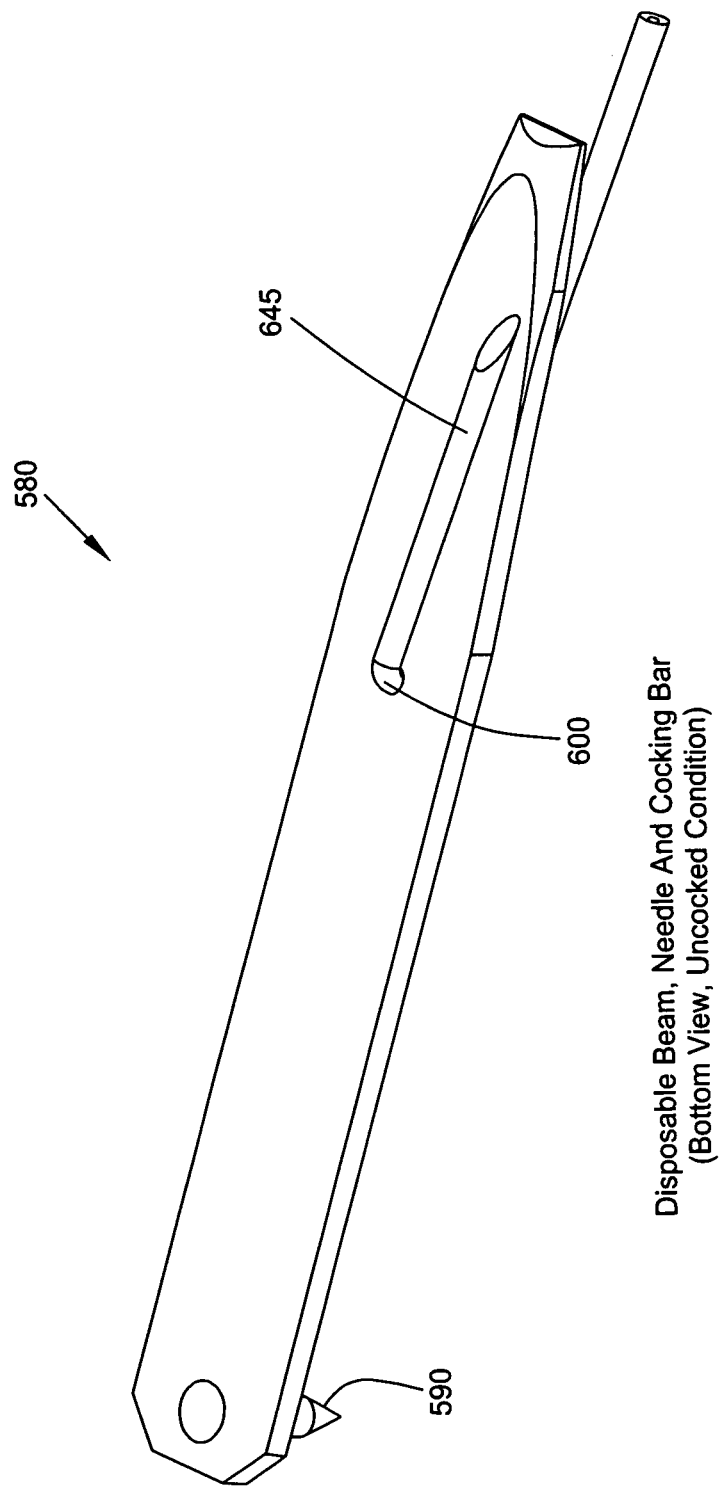

Looking next at FIGS. 23-25, there is shown another novel microfracture instrument 505 formed in accordance with the present invention. Microfracture instrument 505 generally comprises a hollow shaft 510 having a distal end 515, a proximal end 520, and a side window 525 formed adjacent to distal end 515. A pair of holes 527 are formed in hollow shaft 510 adjacent to side window 525. A handle 530 is secured to proximal end 520 of hollow shaft 510. A trigger 535 is pivotally connected to handle 530 via a pivot pin 540. An opening 542 is formed in handle 530 proximal to pivot pin 540, and receives a screw 543 therein, for reasons which will hereinafter be disclosed.

A hollow trigger tube 545 is slidably mounted within hollow shaft 510. Hollow trigger tube 545 comprises a distal end 550, a proximal end 555, and a side opening 560 adjacent to distal end 550. Hollow trigger tube 545 includes a laterally projecting section 565 intermediate its side opening 560. A notch 567 is formed at the distal end of trigger tube 545. A pair of screws 570 (only one of which is seen in FIG. 23) connects the proximal end of hollow trigger tube 545 to trigger 535. By way of example but not limitation, the top end of trigger 535 may be bifurcated, and each upper leg of the trigger may be connected to hollow trigger tube 545 via one screw 570. A compression spring 575 is coaxially mounted on the proximal end of hollow trigger tube 545 and is captured between proximal end 520 of hollow shaft 510 and trigger 535. As a result of this construction, compression spring 575 normally biases hollow trigger tube 545 (and trigger 535) proximally, however, trigger 535 may be used (e.g., by depressing the trigger) so as to urge hollow trigger tube 545 distally.

Still looking now at FIGS. 23-25, microfracture instrument 505 also comprises a beam 580. Beam 580 is disposed within side window 525 of hollow shaft 510 and within side opening 560 of hollow trigger tube 545. The center portion of beam 580 is secured in place via a U-shaped clip 585 which extends through holes 527 formed in hollow shaft 510, with one leg of U-shaped clip 585 being disposed above beam 580 and the other leg of U-shaped clip 585 being disposed below beam 580. A sharp pointed needle 590 projects laterally out of the distal end of beam 580. An opening 600 is formed in beam 580, proximal to the point where U-shaped clip 585 engages beam 580.

A cocking shaft 605 is slidably mounted within hollow trigger tube 545. Cocking shaft 605 comprises a distal end 610 having a groove 615 formed therein, and a proximal end 620 having a cocking knob 625 secured thereto. Cocking knob 625 includes a peripheral groove 630 and a laterally-projecting finger 635. Peripheral groove 630 receives the tip of screw 543 therein, whereby to limit longitudinal movement of cocking knob 625, and hence cocking shaft 605, relative to handle 530. Finger 635 acts as a visual indicator to show the current rotational disposition of cocking shaft 605 within hollow trigger tube 545, as will hereinafter be discussed in further detail.

If desired, an opening 640 may extend through cocking shaft 605 and cocking knob 625, e.g., so as to permit an endoscope to be advanced through microfracture instrument 505 and facilitate visualization of the surgical site. By passing an endoscope through opening 640 in microfracture instrument 505, the endoscope and microfracture instrument can both use a single arthroscopic portal. This can be helpful in various situations, e.g., where the anatomy limits the availability (number and placement) of the access portals. Furthermore, by providing an endoscope-receiving opening 640 in the microfracture instrument 505, the endoscope can be automatically positioned relative to the surgical site simply by positioning of the microfracture instrument relative to the surgical site. This can help reduce the number of "hands" needed to perform the arthroscopic microfracture surgery, and can help ensure that the endoscope is always properly directed at the surgical field.

If desired, the endoscope can be inserted into opening 640 of microfracture instrument 505 in the operating room, e.g., just prior to the commencement of the microfracture procedure or even during the microfracture procedure itself. Alternatively, microfracture instrument 505 could be manufactured so that the endoscope is inserted into opening 640 before the instrument leaves the factory.

A cocking bar (or wire) 645 connects cocking shaft 605 to beam 580. More particularly, cocking bar 645 comprises a J-shaped element which passes through opening 600 in beam 580 and which is secured in groove 615 of cocking shaft 605. As a result of this construction, rotation of cocking shaft 605 (e.g., applied via cocking knob 625) applies a rotational force to the proximal end of beam 580 via the J-shaped cocking bar 645.

It should be appreciated that microfracture instrument 505 may be reusable or disposable.

Furthermore, microfracture instrument 505 may be partially disposable. More particularly, if desired, beam 580, needle 590 and J-shaped cocking bar 645 can be replaced (as a complete subassembly) by simply removing U-shaped clip 585 and installing a replacement sub-assembly (consisting of a new beam 580, a new needle 590 and a new J-shaped cocking bar 645). This approach allows the majority of microfracture instrument 505 to be re-used while still permitting a new subassembly (i.e., a new beam 580, a new needle 590 and a new J-shaped cocking bar 645) to be supplied for each procedure.

Furthermore, the ability to replace beam 580, a needle 590 and a J-shaped cocking bar 645 also permits the microfracture instrument 505 to be quickly modified for different applications, e.g., where harder bone is to be penetrated, a beam 580 having a greater spring factor can be employed. Hollow shaft 510 may have two or more sets of holes 527, thereby allowing U-shaped clip 585 to be inserted in multiple positions. This changes the ratio of the length of beam 580 in front of U-shaped clip 585 to the length of beam 580 behind U-shaped clip 585. The result is a change in total travel of needle 590 and the resulting force it applies on the bone.

Novel microfracture instrument 505 permits microfracture therapy to be arthroscopically applied to a bone surface, even where that bone surface is set at an angle to the axis of approach and/or where it might otherwise be difficult or impossible to use a conventional pick or awl to perform the microfracture surgery.

The use of microfracture instrument 505 typically starts with the instrument in its "at rest" condition, i.e., with the distal end of beam 580 set in notch 567 of hollow trigger tube 545, trigger 535 released, and cocking knob 625 set so that its finger 635 points down and groove 615 of cocking shaft 605 points upward. See FIGS. 23 and 24.

Figure 26:
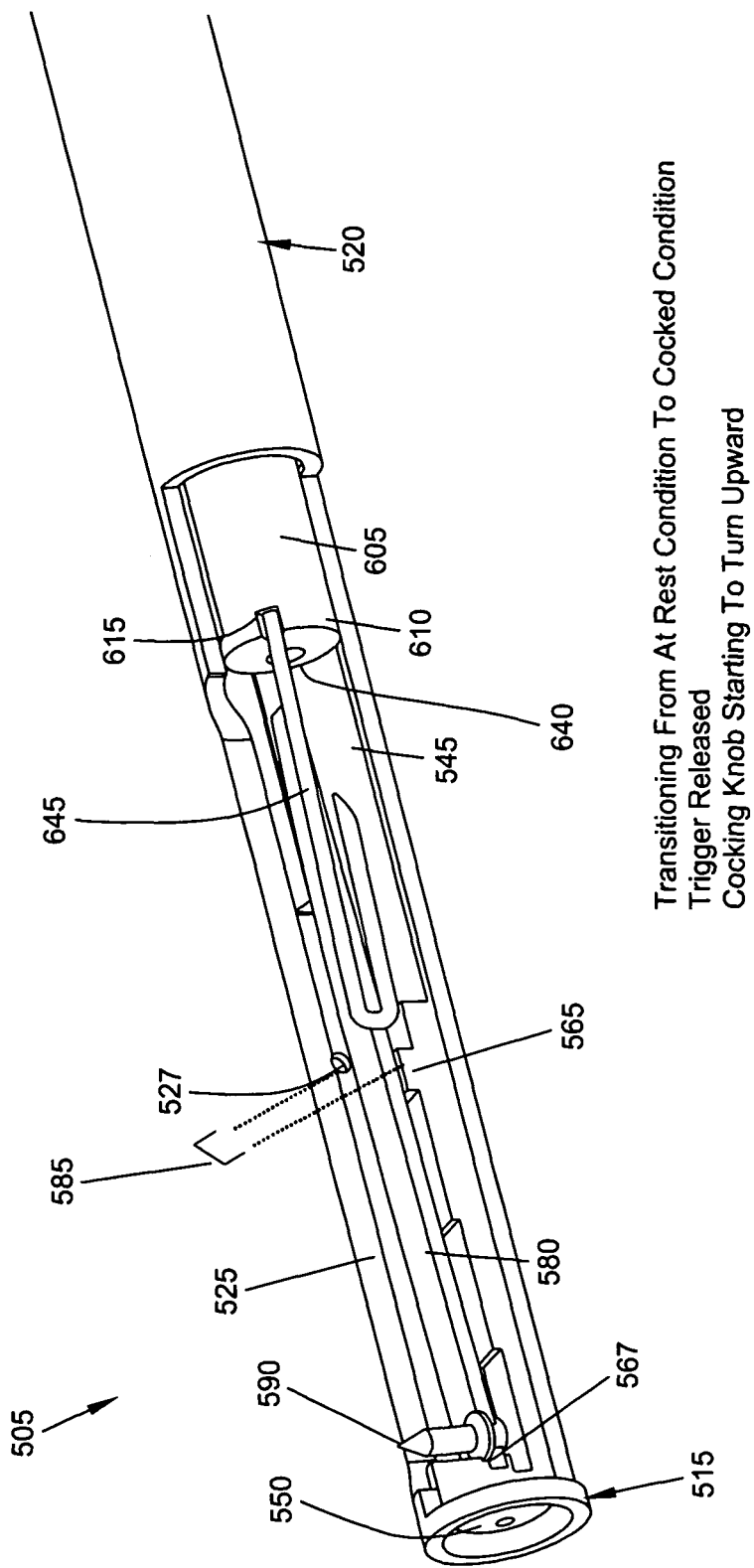

Next, cocking knob 625 is rotated. This in turn causes cocking shaft 605 to be rotated. Cocking knob 625 is rotated to the point where its finger 635 points upward and groove 615 of cocking shaft 605 faces downward. As this occurs, the proximal end of cocking bar 645 (which is disposed in groove 615 of cocking shaft 605) is also rotated, which applies a torsional force to the proximal end of beam 580, thereby flexing beam 580. See FIGS. 26 and 27.

Figure 27:
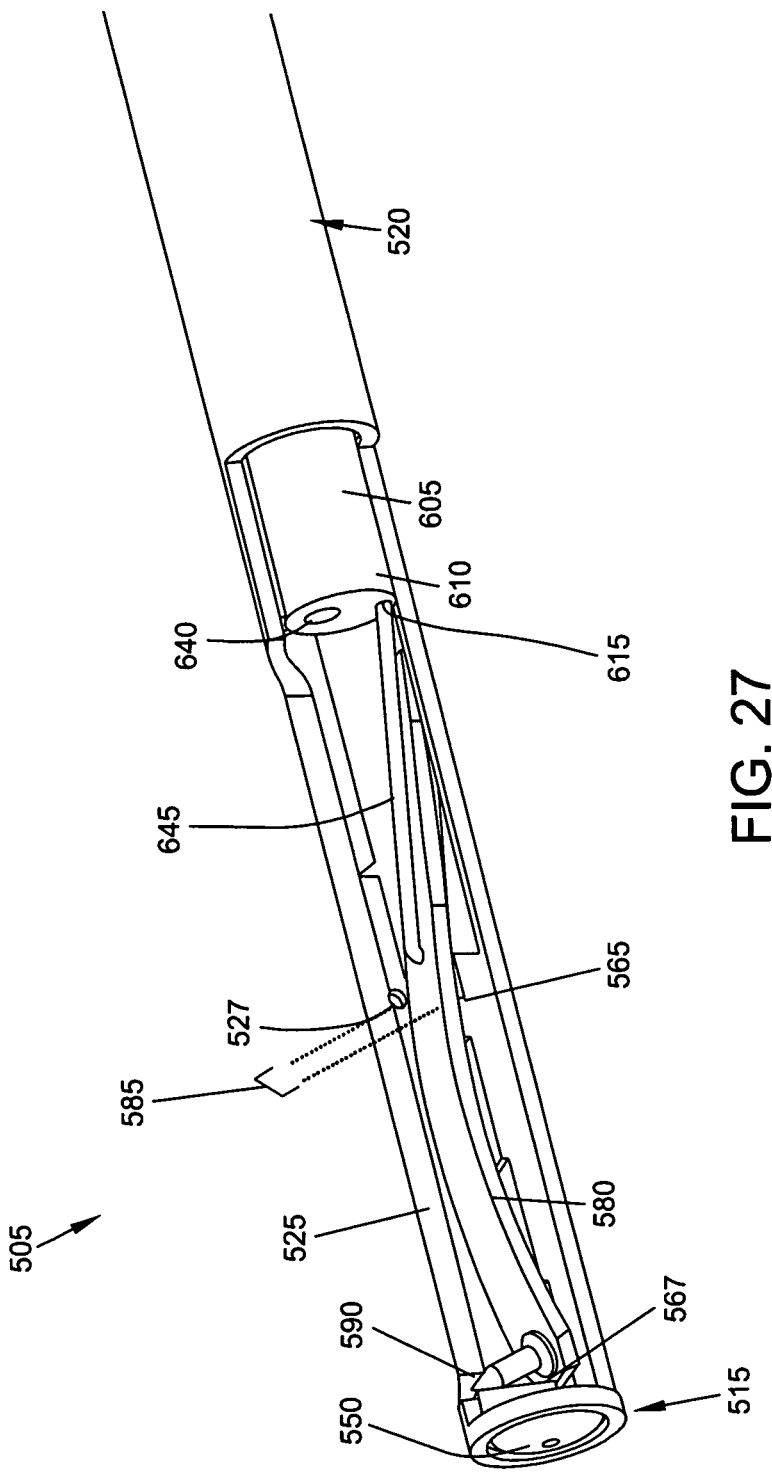

It should be appreciated that, due to the nature and configuration of beam 580, and due to the manner in which beam 580 is simultaneously supported (i) in its midsection (via engagement with U-shaped clip 585), (ii) at its distal end (via engagement with notch 567), and (iii) at its proximal end (via J-shaped cocking bar 645 which extends between beam opening 600 and cocking shaft groove 615), the microfracture instrument 505 will be in a stable condition when cocking shaft 605 is disposed so that groove 615 is oriented fully up (FIGS. 23 and 24) or fully down (FIG. 27).

Thus, when cocking knob 625 is rotated to the point where its finger 635 points upward and groove 615 of cocking shaft 605 faces downward, the microfracture instrument will be in a stable condition, with its beam 580 flexed so as to store potential energy in beam 580.

At this point, the device is cocked.

Microfracture instrument 505 is then manipulated so that its sharp pointed needle 590 is disposed opposite the site of the desired microfracture therapy.

Figure 28:
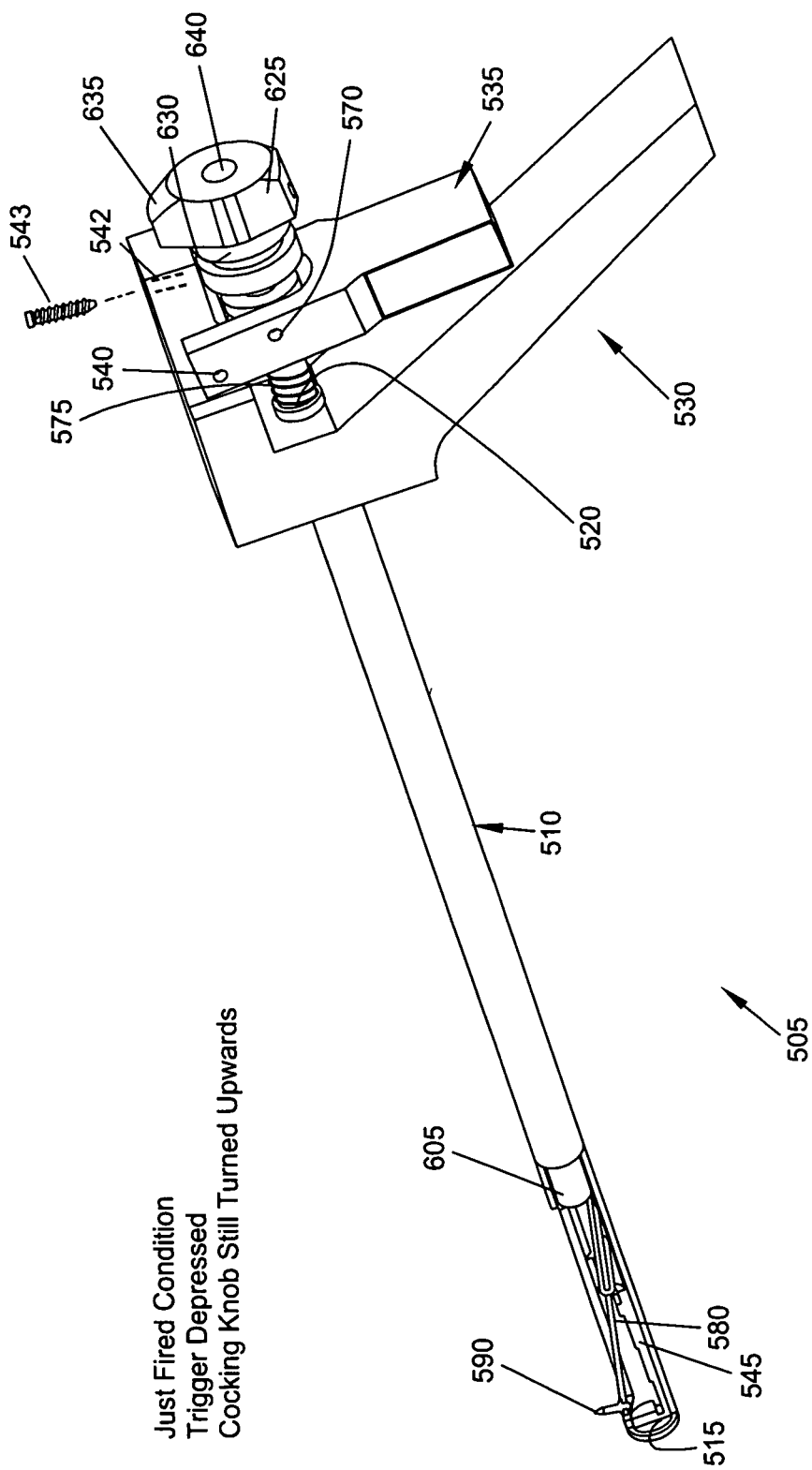

When microfracture instrument 505 is in proper position, trigger 535 is depressed so that hollow trigger tube 545 moves distally. This action releases the distal end of beam 580 from notch 567, thereby permitting flexed beam 580 to straighten, which causes the distal end of beam 580 to be driven laterally. As the distal end of beam 580 is driven laterally, sharp pointed needle 590 is driven laterally out of instrument 505 and into the adjacent bone, whereby to create a desired microfracture. See FIG. 28.

Figure 29:
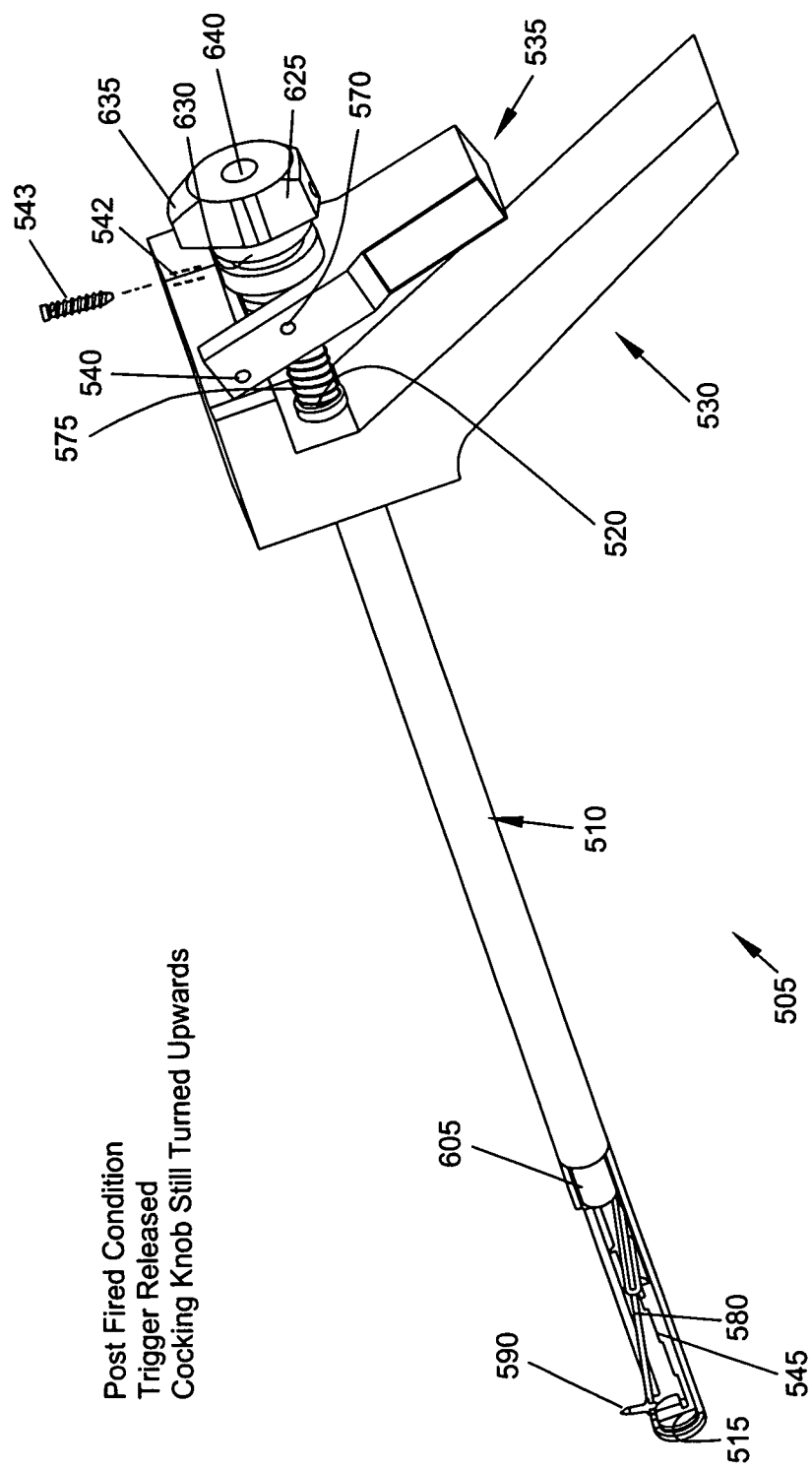

Then trigger 535 may be released. See FIG. 29.

When it is desired to form another microfracture, instrument 505 must first be restored to its "at rest" condition, then re-cocked, and finally re-fired.

Figure 30:
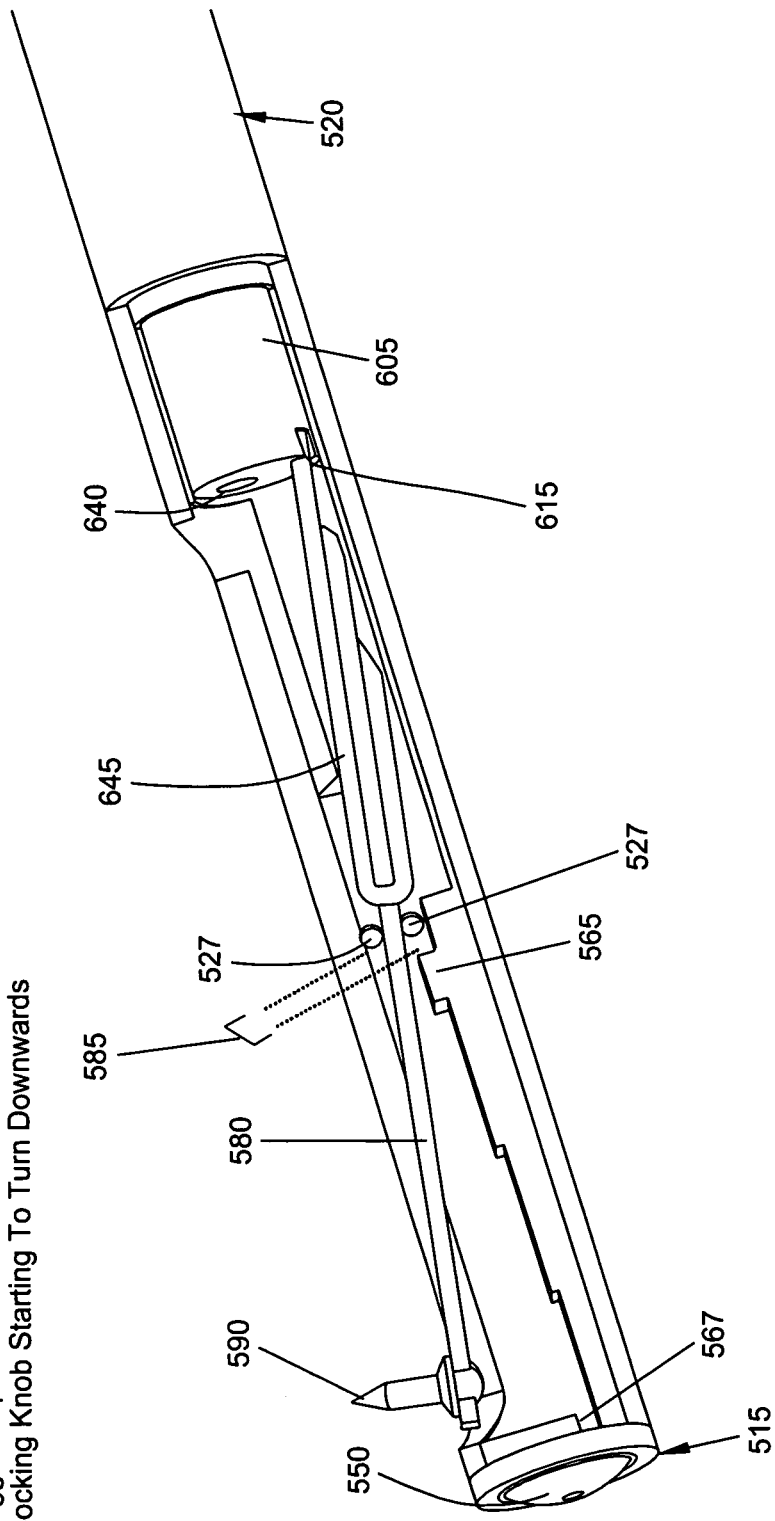
Figure 31:
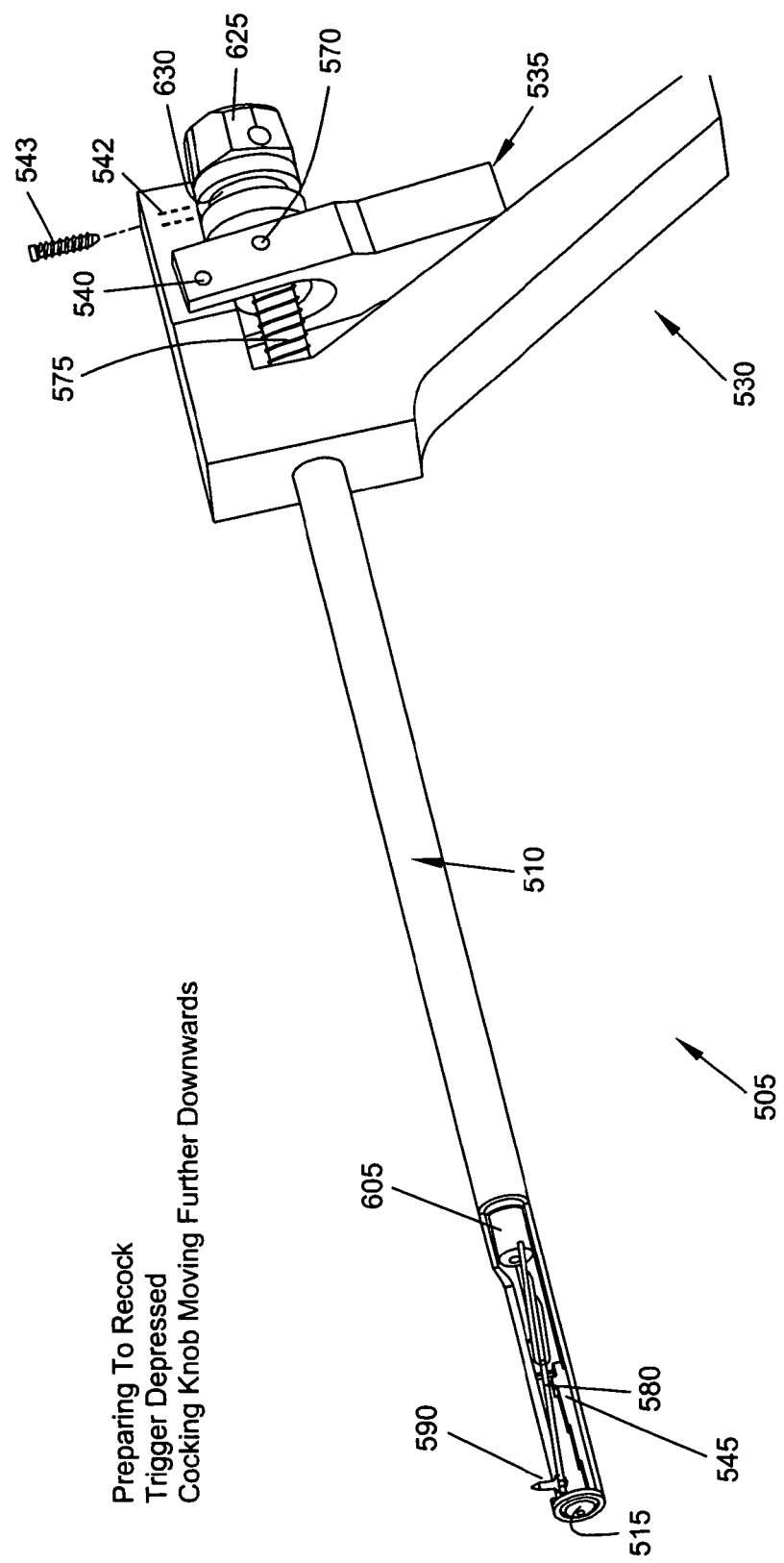
Figure 32:
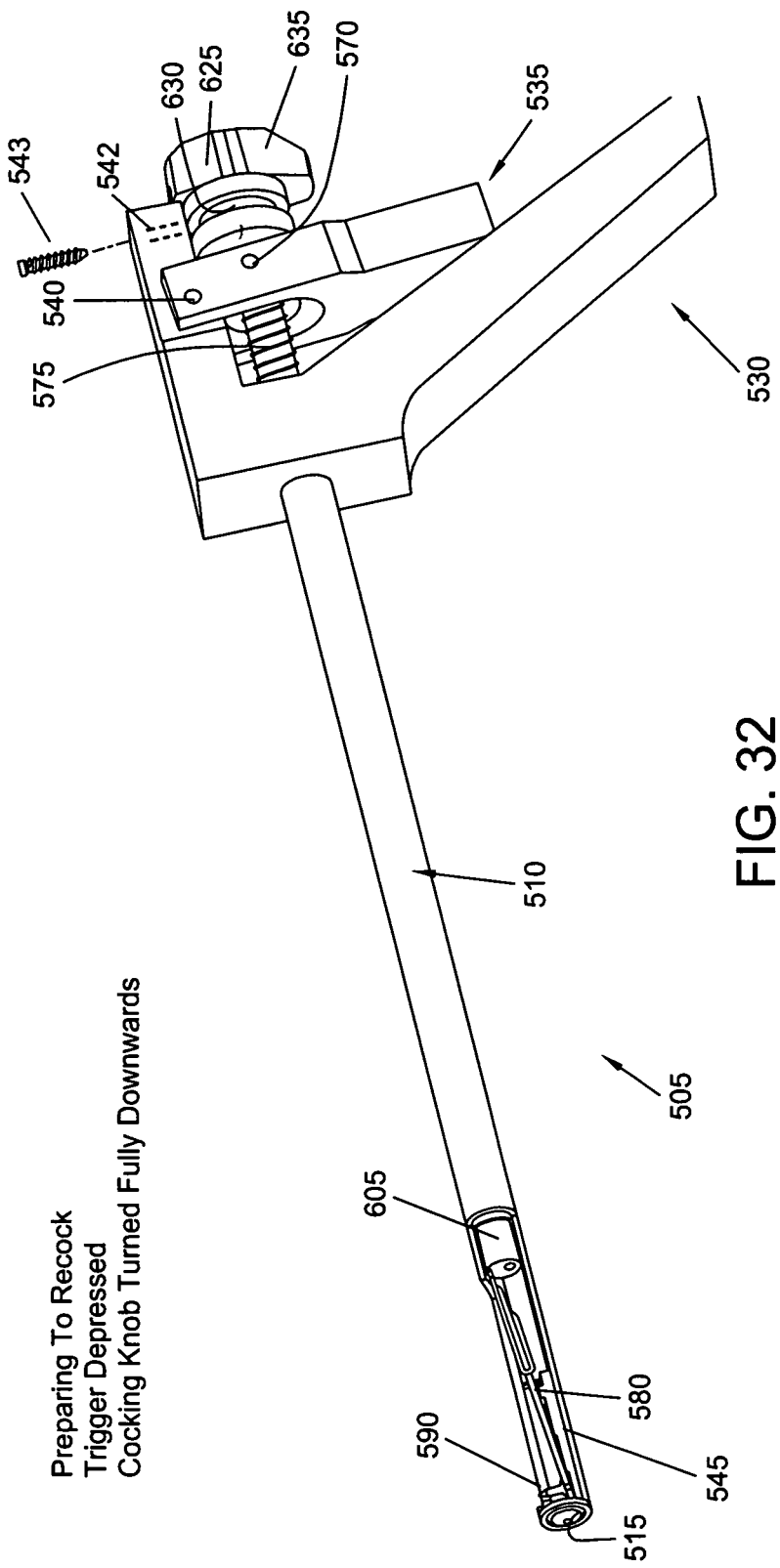
Figure 33:
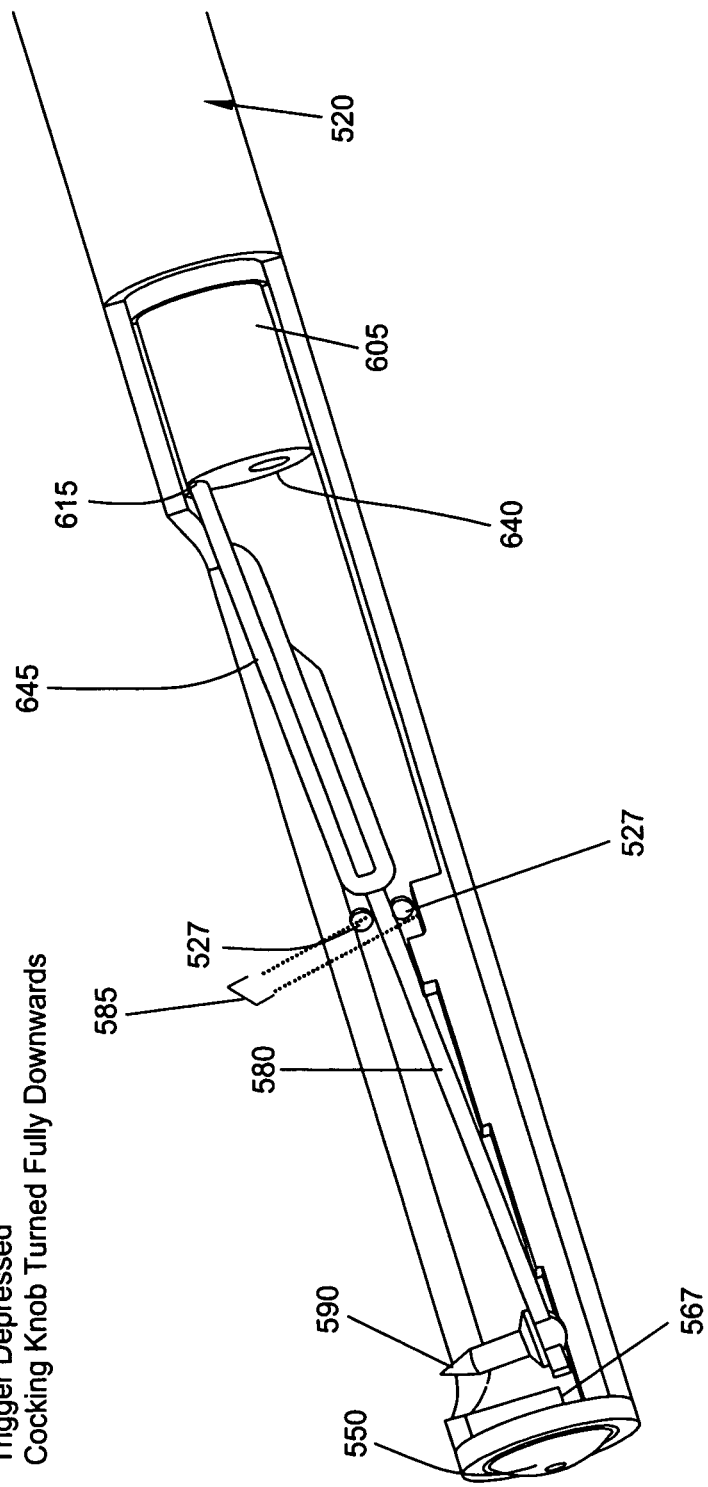
Figure 34:
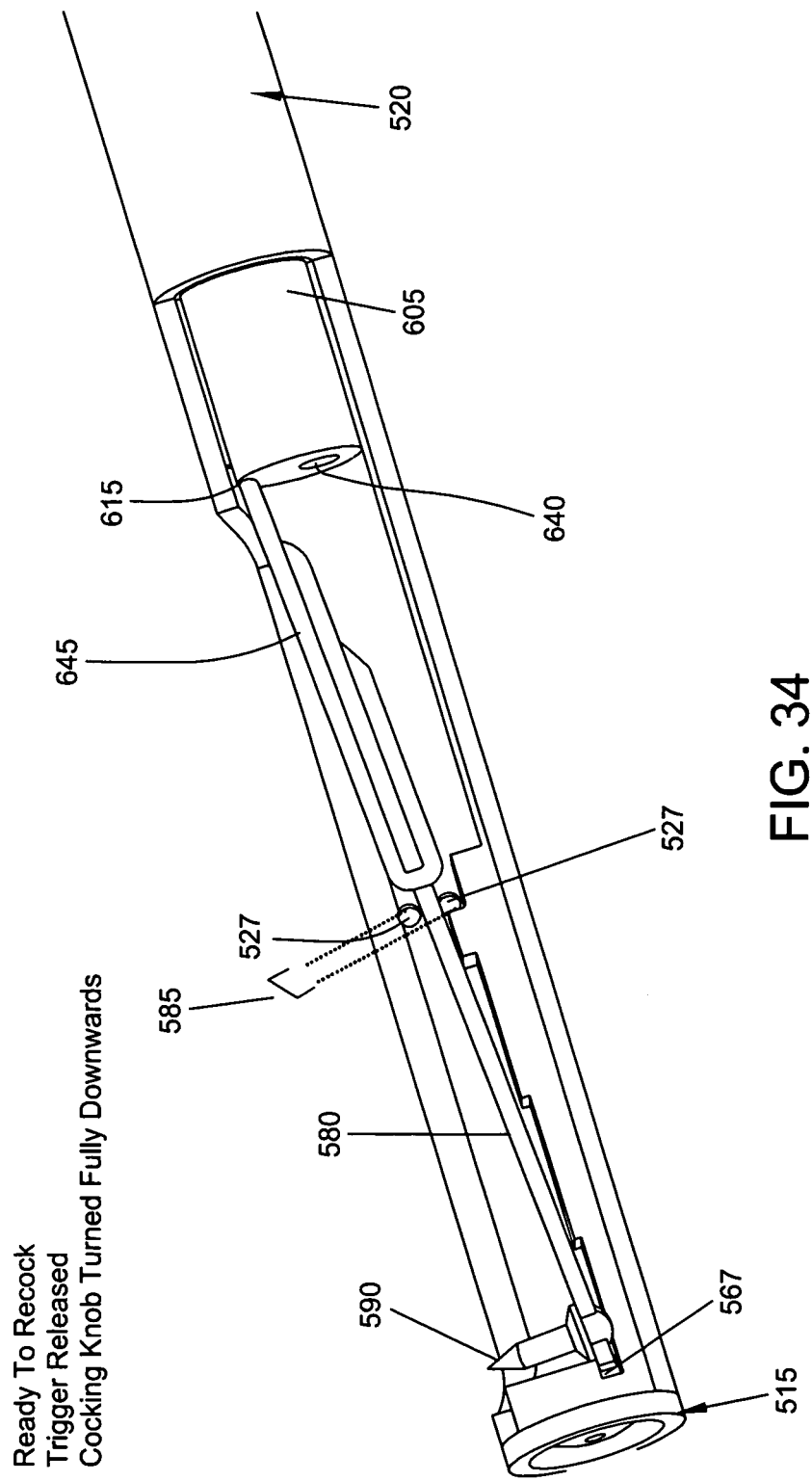

The instrument is restored to its "at rest" condition by first re-depressing trigger 535. See FIG. 30. Then cocking knob 625 is rotated so that its finger 635 is restored to its downward position and groove 615 of cocking shaft 605 once again faces upward. This causes beam 580 to return to its original condition where the distal end of the beam is lowered and the proximal end of the beam is raised. See FIGS. 30-32. Then trigger 535 is released, so that hollow trigger tube 545 moves proximally and the distal end of beam 580 is re-captured within notch 567. At this point the instrument has fully returned to its "at rest" condition shown in FIGS. 23 and 24.

The microfracture instrument may then be re-cocked, and thereafter fired, according to the foregoing sequence.

Thus it will be seen that the microfracture instrument of the present invention comprises an apparatus which provides the ability to store, and remotely release, controlled amounts of captured kinetic energy. The precise amount of energy stored and subsequently released can be regulated by the particular construction of beam 580 (e.g., the choice of materials used, the configuration of the beam, the dimensions of the beam, etc.). Furthermore, the amount of energy stored and released could be regulated by utilizing an alternative form of cocking mechanism, e.g., one which permits the user to determine the precise amount of beam deflection used to drive needle 590 (such as a ratchet mechanism). It will be appreciated that the approach used by the present invention is fundamentally different from the "hammer hit" pick or awl of current microfracture techniques, since the present invention permits a controlled amount of energy to be stored and remotely released.

If desired, the distal end of microfracture instrument 505 may be formed with a flexible configuration. Such a construction can permit microfracture instrument 505 to better conform to the particulars of a treatment site or to extend the reach of the instrument without the need to fully distract a joint.

Furthermore, the distal end of shaft 510 can be provided with a locator needle extending laterally of the microfracture instrument 505. This locator needle can be placed in a previously-placed fracture hole so as to set the location of a subsequent fracture hole. This arrangement can be used so as to ensure a known spacing between various fracture holes.

Additionally, beam 580 can be provided with more than one needle, thus allowing for the placement of multiple fracture holes with one "firing" of the instrument. Where more than one needle 590 is provided, the multiple needles can be arranged in various configurations, e.g., linear, crossed, etc.

If desired, beam 580 can be formed with a slight recess on its underside so as to form a natural seat for J-shaped cocking bar 645 when the microfracture instrument is placed in its cocked position (FIG. 27). This construction has the advantage that it can provide tactile feedback to the user when the J-shaped cocking bar 645 seats in the recess, thereby confirming for the user that the microfracture instrument has been placed in its cocked state.

If desired, the needle of the microfracture instrument may be adapted to deliver a therapeutic agent which induces cartilage growth.

Figure 35:
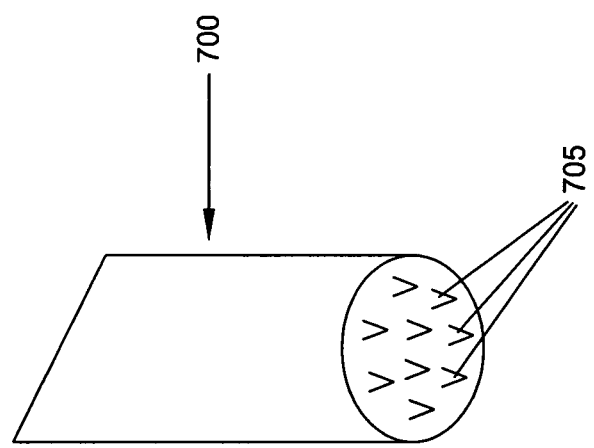
FIG. 35 is a schematic view showing a distal end of another form of needle.

Furthermore, it should also be appreciated that the needle of the microfracture instrument may be configured to provide a plurality of sharp points. Thus, for example, in FIG. 35, there is shown a needle 700 comprising a plurality of sharp points 705 for applying microfracture therapy to a bone. This configuration can be advantageous where it is desired to apply a plurality of microfractures with a single impact.

Figure 36A:
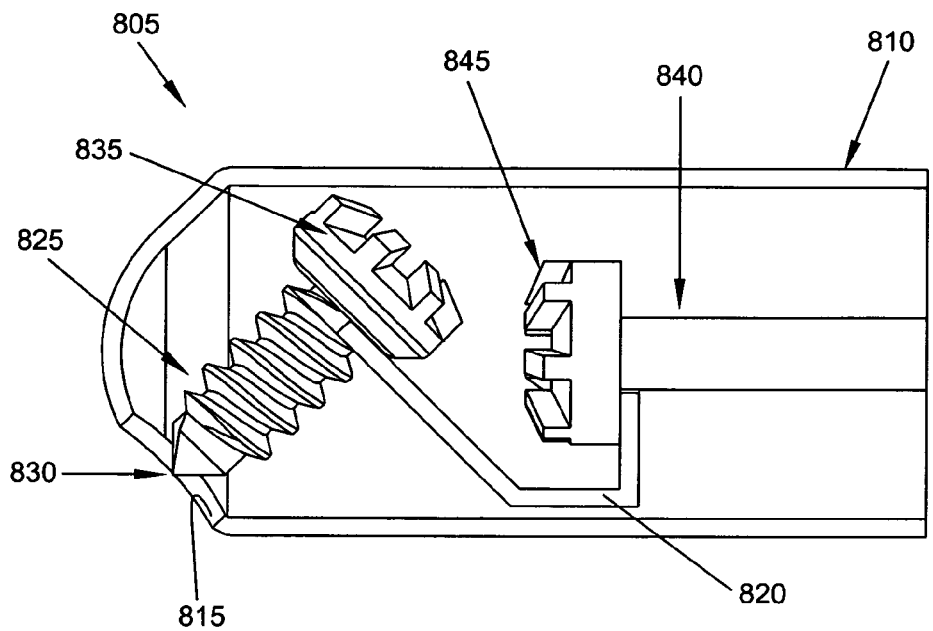
FIGS. 36A, 36B, 37A, 37B, 38 and 39 are schematic views showing a seventh microfracture instrument formed in accordance with the present invention.
Figure 36B:
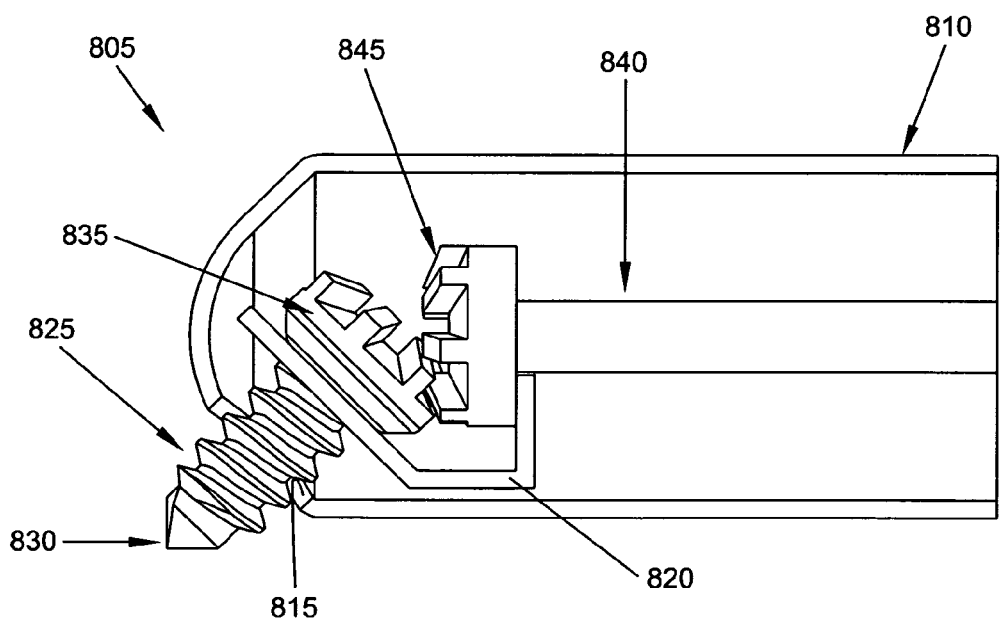
Figure 37A:
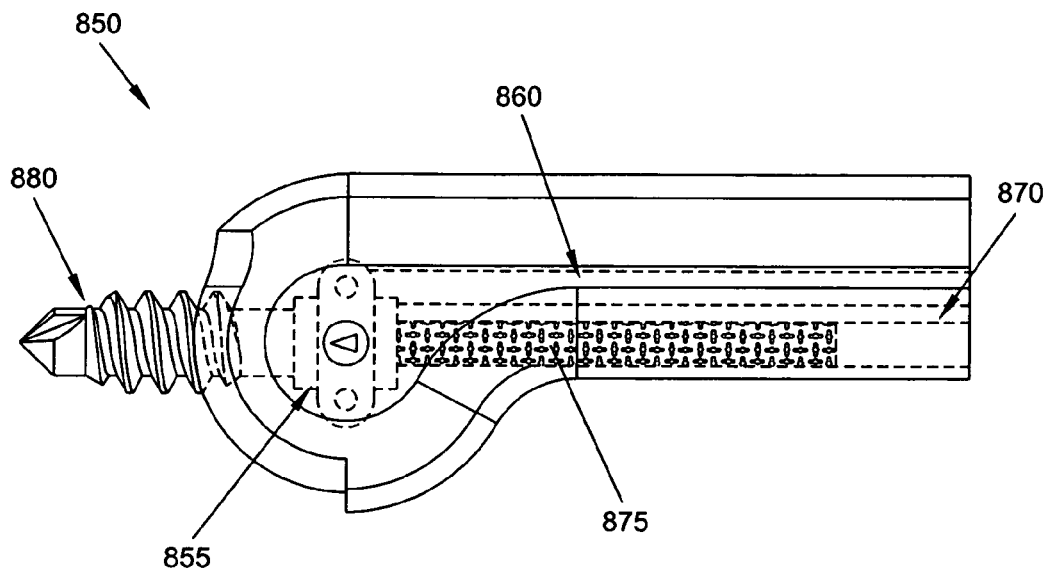
Figure 37B:
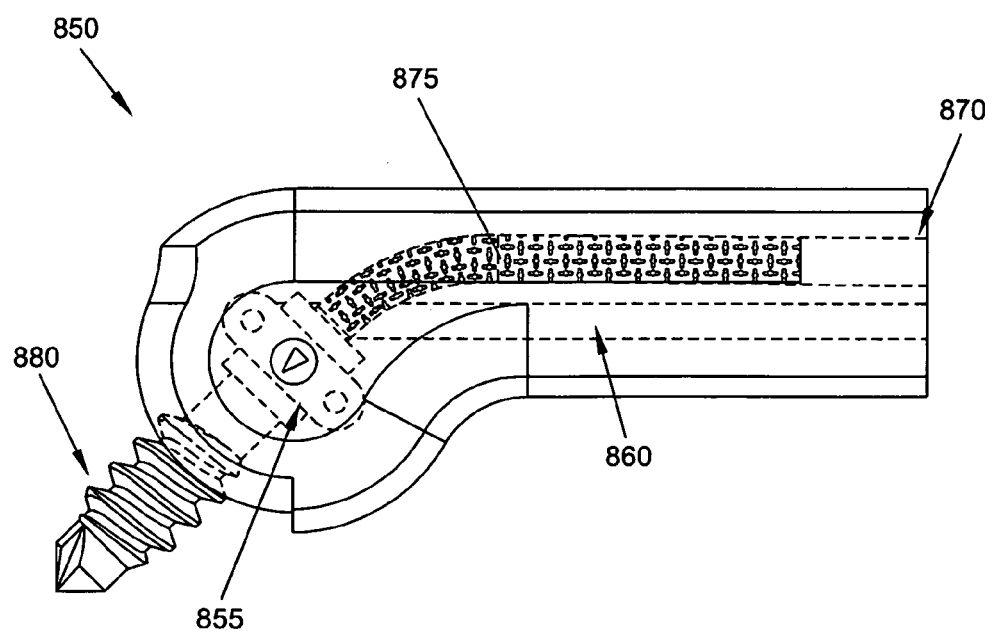
Figure 38:
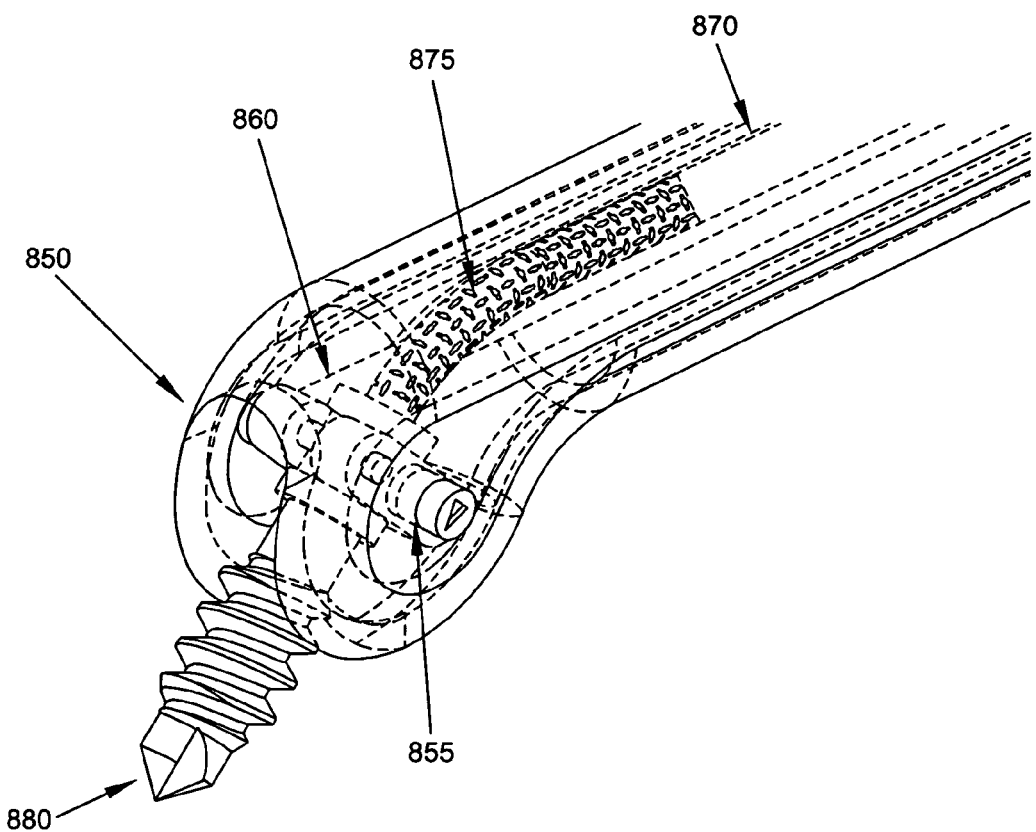
Figure 39:
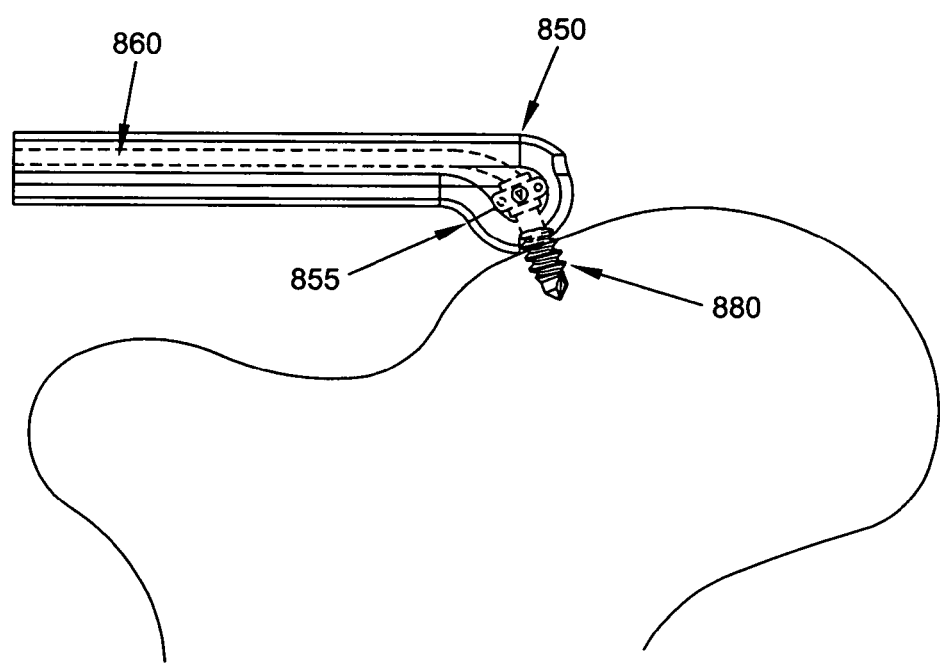

Looking next at FIGS. 36A and 36B, there is shown another novel microfracture instrument 805 also formed in accordance with the present invention. Microfracture instrument 805 is intended to penetrate a bone with a drilling action rather than with an impact action as is the case with the microfracture instruments disclosed above.

To this end, microfracture instrument 805 generally comprises an elongated shaft 810 having an opening 815 formed in its distal end. A bracket 820 is disposed within elongated shaft 810 adjacent to opening 815. Bracket 820 serves to rotatably support a drill element 825 extending through opening 815. Drill element 825 in turn comprises a drill tip 830 and a geared head 835. Geared head 835 is driven by a drive shaft 840. More particularly, drive shaft 840 has a geared distal end 845 for engaging the geared head 835 of drill element 825.

On account of the foregoing construction, elongated shaft 810 can be used to advance microfracture instrument 805 so that its drill element 825 is located adjacent to the bone site which is to be microfractured, and then drive shaft 840 can be rotated so as to turn drill element 825 into the bone, whereby to created the desired microfracture. This process can be repeated as many times as desired until the desired degree of microfracture has been achieved.

FIGS. 37A, 37B, 38 and 39 show a related construction. More particularly, with the construction shown in FIGS. 36A and 36B, drill element 825 extends at a fixed angle relative to the longitudinal axis of elongated shaft 810. The construction shown in FIGS. 37A, 37B, 38 and 39 allows the angle of the drill element to be adjusted relative to the longitudinal axis of the elongated shaft.

More particularly, in FIGS. 37A, 37B, 38 and 39 there is shown a microfracture instrument 850 which has a mount 855 pivotally disposed at its distal end. Mount 855 is pivoted by pushing or pulling on one or more control rods or lines 860 so as to adjust the angular position of mount 855 relative to the longitudinal axis of the microfracture instrument. Microfracture instrument 850 also comprises a drive shaft 870 which has a flexible distal end 875 extending through mount 855, such that adjustment of the angular position of mount 855 results in adjustment of the angular position of flexible distal end 875 of drive shaft 870. Flexible distal end 875 of drive shaft 870 supports a drill element 880.

On account of the foregoing construction, the elongated shaft of microfracture instrument 850 can be used to position drill element 880 adjacent to the bone site which is to be microfractured, mount 855 can be moved (via one or more control rods or lines 860) so as to direct the drill element toward the bone surface, and then drive shaft 870 can be rotated so as to turn drill element 880 into the bone, whereby to created the desired microfracture. Again, this process can be repeated as many times as desired until the desired degree of microfracture has been achieved.

MODIFICATIONS

It will be understood that many changes in the details, materials, steps and arrangements of elements, which have been herein described and illustrated in order to explain the nature of the invention, may be made by those skilled in the art without departing from the scope of the present invention.

What is claimed is:

1. A microfracture instrument for applying microfracture therapy to a bone, the microfracture instrument comprising:
    an elongated shaft comprising a distal end and a proximal end and having a longitudinal axis extending from the distal end to the proximal end;
    a mount comprising an opening having a longitudinal axis extending therethrough, wherein the mount is pivotally disposed at the distal end of the elongated shaft, the mount being configured to pivot relative to the longitudinal axis of the elongated shaft; and
    a drive shaft rotatably mounted to the elongated shaft, the drive shaft comprising a flexible distal end, the flexible distal end extending through the opening in the mount and supporting a drill element thereon, wherein the drill element comprises a sharp distal tip, a body and a longitudinal axis extending between the sharp distal tip and the body;
    wherein pivotally adjusting the mount relative to the longitudinal axis of the elongated shaft results in movement of the flexible distal end of the drive shaft and the drill element supported thereon so as to direct the drill element at a selected angle relative to the longitudinal axis of the elongated shaft, wherein the longitudinal axis of the opening of the mount is aligned with the longitudinal axis of the drill element;
    wherein rotational movement of the drive shaft is configured to move the drill element into the bone.

2. The microfracture instrument according to claim 1 further comprising at least one control rod for pivoting the mount.

3. The microfracture instrument according to claim 1 wherein the drill element comprises screw threads.

4. A microfracture instrument for applying microfracture therapy to a bone, the microfracture instrument comprising:
    an elongated shaft comprising a distal end and a proximal end;
    a needle comprising a body terminating in at least one sharp point, the needle being movably mounted to the distal end of the elongated shaft for movement between an extended position for engaging the bone with the at least one sharp point of the needle and a retracted position for withdrawing the at least one sharp point of the needle from the bone; and
    a drive shaft movably mounted to the elongated shaft, the drive shaft being connected to the body of the needle so that movement of the drive shaft relative to the elongated shaft moves the needle between its extended position and its retracted position;
    wherein the elongated shaft comprises a longitudinal axis extending between its distal end and its proximal end, wherein the needle comprises a longitudinal axis extending between its at least one sharp point and its body, and further wherein the longitudinal axis of the needle is disposed at an angle to the longitudinal axis of the elongated shaft;
    wherein the drive shaft is adapted to move rotationally relative to the elongated shaft in order to move the needle between its extended position and its retracted position;
    wherein the drive shaft comprises a first gear member, and wherein the body of the needle comprises a second gear member for engaging the first gear member, whereby rotation of the drive shaft causes rotation of the needle.

* * * * *